United States Patent
Wakai

(10) Patent No.: US 10,561,381 B2
(45) Date of Patent: Feb. 18, 2020

(54) MEDICAL IMAGE DIAGNOSTIC APPARATUS, AND MEDICAL IMAGE PROCESSING APPARATUS

(71) Applicant: TOSHIBA MEDICAL SYSTEMS CORPORATION, Otawara-Shi (JP)

(72) Inventor: Satoshi Wakai, Nasushiobara (JP)

(73) Assignee: Canon Medical Systems Corporation, Otawara-shi (JP)

(*) Notice: Subject to any disclaimer, the term of this patent is extended or adjusted under 35 U.S.C. 154(b) by 429 days.

(21) Appl. No.: 15/616,293

(22) Filed: Jun. 7, 2017

(65) Prior Publication Data
US 2017/0347980 A1 Dec. 7, 2017

(30) Foreign Application Priority Data

Jun. 7, 2016 (JP) .................. 2016-113347
Jun. 1, 2017 (JP) .................. 2017-109213

(51) Int. Cl.
*A61B 6/00* (2006.01)
*A61B 6/12* (2006.01)

(52) U.S. Cl.
CPC .............. *A61B 6/12* (2013.01); *A61B 6/4441* (2013.01); *A61B 6/463* (2013.01); *A61B 6/485* (2013.01); *A61B 6/503* (2013.01); *A61B 6/504* (2013.01); *A61B 6/5217* (2013.01); *A61B 6/5223* (2013.01); *A61B 6/5235* (2013.01); *A61B 6/5247* (2013.01); *A61B 6/5288* (2013.01); *A61B 6/5294* (2013.01)

(58) Field of Classification Search
CPC ............ A61B 6/12; A61B 6/441; A61B 6/463
See application file for complete search history.

(56) References Cited

U.S. PATENT DOCUMENTS

| 6,556,695 | B1 | 4/2003 | Packer et al. |
| 2006/0095085 | A1 | 5/2006 | Marcus et al. |
| 2006/0190045 | A1 | 8/2006 | Marcus et al. |
| 2014/0205145 | A1 | 7/2014 | Jacobs et al. |

FOREIGN PATENT DOCUMENTS

| JP | 2007-500550 | 1/2007 |
| JP | 4965042 | 7/2012 |
| JP | 2014-140742 | 8/2014 |

*Primary Examiner* — Joseph M Santos Rodriguez
(74) *Attorney, Agent, or Firm* — Oblon, McClelland, Maier & Neustadt, L.L.P.

(57) ABSTRACT

In one embodiment, a medical image diagnostic apparatus includes a memory circuit; a display; and processing circuitry configured to acquire medical images of an object at respective time phases, detect respective positions of a treatment device in the medical images, acquire biological information from the medical images, compute biological indexes indicating degree of a treatment effect for the respective time phases based on the biological information, cause the memory circuit to store the biological indexes and the respective positions of the treatment device in the medical images such that each biological index is associated with a position of the treatment device in a medical image, from which the biological information corresponding to the each biological index is acquired, for the respective time phases, and cause the display to display each position of the treatment device and a biological index associated with the each position of the treatment device.

15 Claims, 18 Drawing Sheets

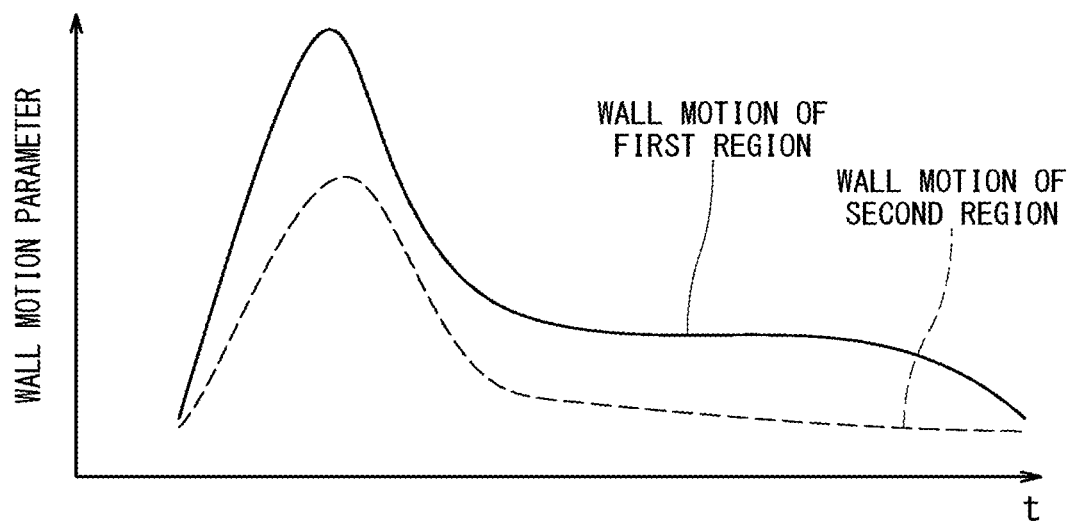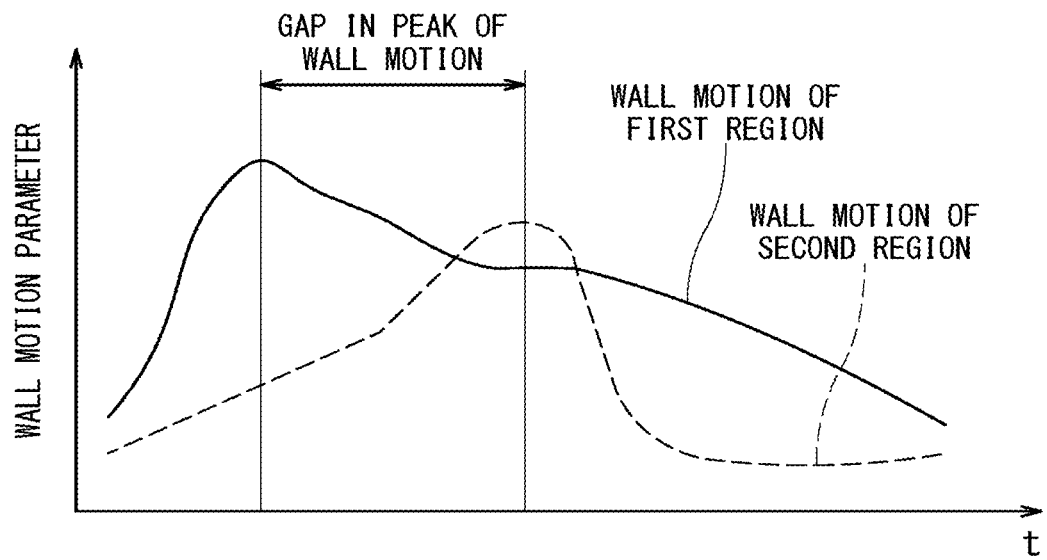
FIG. 16

MEDICAL IMAGE DIAGNOSTIC APPARATUS, AND MEDICAL IMAGE PROCESSING APPARATUS

CROSS-REFERENCE TO RELATED APPLICATION

This application is based upon and claims the benefit of priority from Japanese Patent Application No. 2016-113347, filed on Jun. 7, 2016, and Japanese Patent Application No. 2017-109213, filed on Jun. 1, 2017 the entire contents of all of which are incorporated herein by reference.

FIELD

Embodiments described herein relate generally to a medical image diagnostic apparatus and a medical image processing apparatus.

BACKGROUND

In an interventional operation, inside of a patient's body is time-sequentially imaged by a medical image diagnostic apparatus such as an X-ray fluoroscopic-imaging apparatus in real time, and an operating surgeon inserts a treatment device such as a catheter into the inside of the patient' s body while referring to the images of the inside of the patient's body being time-sequentially displayed. Since it is possible to non-invasively remedy, e.g., a blood vessel of a heart or a brain in an interventional operation, an interventional operation has come to be applied to various types of operations.

For instance, in the case of implanting a lead-wire tip of a pacemaker used for treating arrhythmia in a heart, an interventional operation is applied. A treatment effect of a pacemaker largely depends on an implanted position of a pacemaker. In conventional technology, a position where a lead-wire tip should be implanted is determined while biological information of a patient is being monitored during an interventional operation, and thus, it is not easy to determine an appropriate position where the lead-wire tip should be implanted.

BRIEF DESCRIPTION OF THE DRAWINGS

In the accompanying drawings:

FIG. 16 is a schematic diagram illustrating a method of computing a biological index on the basis of a wall motion parameter in the second embodiment;

DETAILED DESCRIPTION

Hereinafter, respective embodiments of medical image diagnostic apparatuses and medical image processing apparatuses will be described by referring to the accompanying drawings.

In one embodiment, a medical image diagnostic apparatus includes: a memory circuit; a display; and processing circuitry configured to acquire medical images of an object at respective time phases, detect respective positions of a treatment device in the medical images, acquire biological information from the medical images, compute biological indexes, each of which indicates degree of a treatment effect, for the respective time phases based on the biological information, cause the memory circuit to store the biological indexes and the respective positions of the treatment device in the medical images in such a manner that each biological index is associated with a position of the treatment device in a medical image, from which the biological information corresponding to the each biological index is acquired, for the respective time phases, and cause the display to display each position of the treatment device and a biological index associated with the each position of the treatment device.

Hereinafter, viewpoints of the present inventor will be described prior to descriptions of embodiments of the present invention.

Arrhythmia is disease in which the heart rate becomes abnormal, systole and diastole of ventricles and atria becomes asynchronous, and thus sufficient amount of blood is not pumped from the heart to the whole body. A remedy method called cardiac resynchronization therapy (CRT) is applied as treatment for such disease.

CRT is treatment aimed to recover synchronization between atria and ventricles regarding systole and diastole by implanting a treatment device such as a pacemaker inside a patient's body. A pacemaker normalizes asynchronous systole by generating electric current from its lead-wire tip. In order to normalize systole, it is preferable to implant its lead-wire such that the lead-wire tip is located at the optimal position.

In conventional technology, an operating surgeon seeks the optimal implant position of a lead-wire tip for each patient while moving the lead-wire attached to a tip of catheter and observing an electrocardiogram during the interventional operation, which electrocardiogram varies due to electric current outputted from the lead-wire. Thus, determination of an implant position of a lead-wire tip in the heart largely depends on knowledge, skills, and experience of an operating surgeon in conventional technology, which is one of the factors that a surgical time is prolonged.

Hereinafter, problems of the above-described conventional technology will be more specifically described from the viewpoints of the present inventor by referring to FIG. 1.

Figure 1:
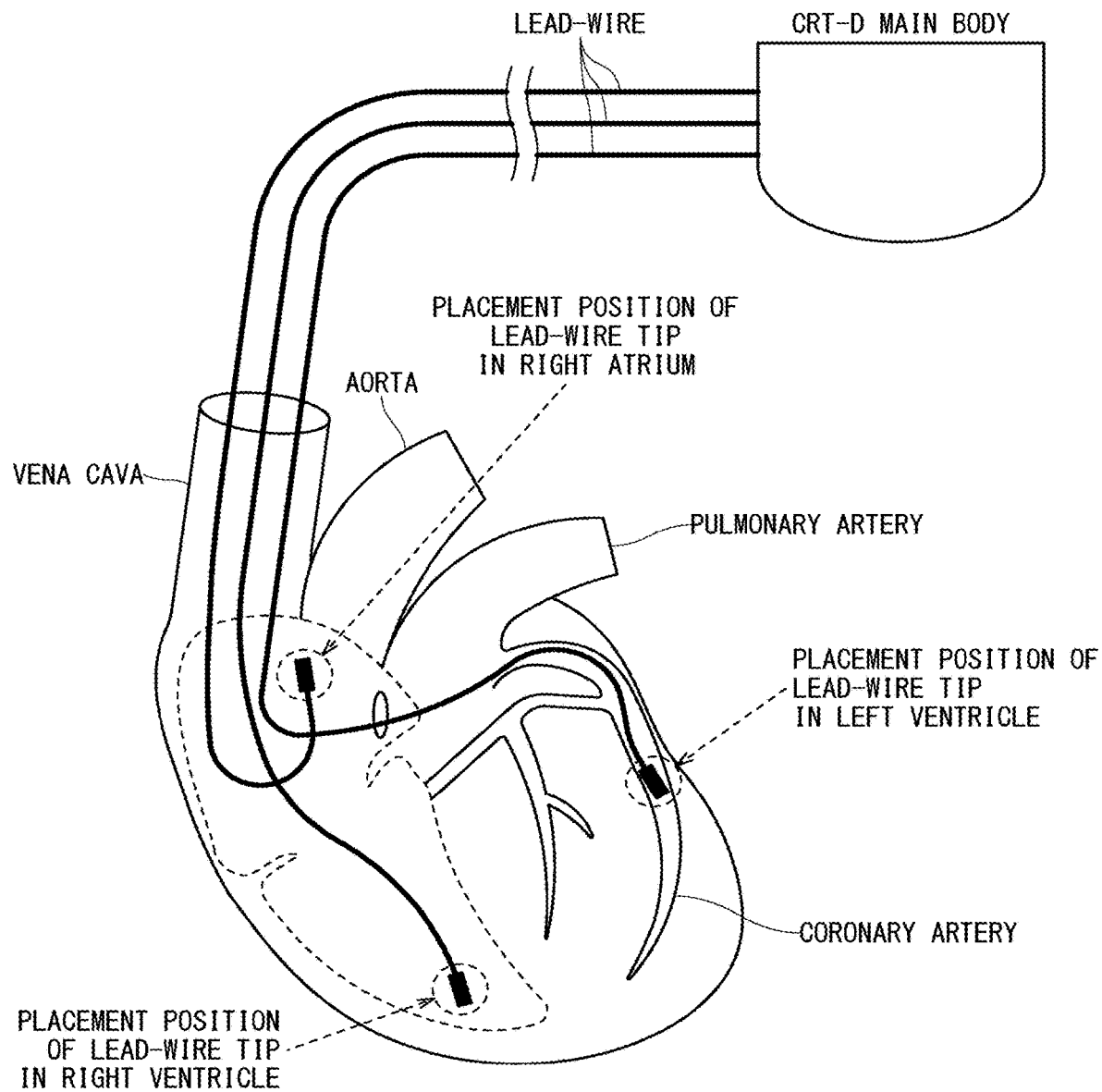
FIG. 1 is a schematic diagram illustrating arrangement of lead-wires in CRT.

FIG. 1 is a schematic diagram illustrating arrangement of lead-wires in CRT. As shown in FIG. 1, a description will be given of a case where three lead-wires of a CRT-D (CRT— Defibrillator) is placed in a heart.

The upper right part of FIG. 1 shows a CRT-D main-body, i.e., the entire CRT-D excluding the lead-wires.

As shown in FIG. 1, three lead-wires are extending toward the heart from the CRT-D main-body. The lead-wire tips are placed in the heart with the use of catheters which pass through the subclavian vein. When the lead-wire tips are placed inside the heart of the object P, the CRT-D main-body is implanted in. e.g., the muscle of the chest of the object P.

As shown in FIG. 1, three lead-wire tips extend through the vena cava, one of the three lead-wire tips is placed in the right atrium, another of them is placed in the right ventricle, the other of them is placed in the vein which is called the coronary vein and extends outside the left ventricle.

In conventional technology, for instance, an operating surgeon performs placement of a lead-wire tip in the coronary vein, while monitoring biological information such as an electrocardiogram and diagnosing whether arrhythmia and/or ventricular fibrillation can be appropriately treated by setting a CRT-D main-body. In conventional technology, when an operating surgeon determines that an appropriate treatment effect cannot be obtained judging from the analysis result of the biological information, the operating surgeon determines the optimal placement position of the lead-wire tip by a trial and error approach such as change of the placement position and change of setting of the CRT-D main-body.

That is, in conventional technology, an operating surgeon determines the optimal treatment target position while operating a catheter, observing biological information such as an electrocardiogram and ultrasonic diagnostic images acquired during the interventional operation, and considering a treatment effect obtained by change of the placement position of the lead-wire tip and setting of the CRT-D main-body. Thus, the above-described placement of a treatment device such as a lead-wire tip largely depends on experience and skills of an operating surgeon. Additionally, it is difficult to instantly and accurately predict a treatment effect from biological information which changes depending on a position of a treatment device. Hence, it takes time to determine the placement position of a treatment device such as a placement position of a lead-wire tip, which is one of factors that the surgical time is prolonged.

For those reasons, the present inventor has worked out an innovative configuration which can assist in determination of an appropriate placement position of a treatment device by displaying both of positional information of a medical device and a biological index indicative of a treatment effect computed on the basis of biological information in association with each other.

Hereinafter, a description will be given of medical image diagnostic apparatuses and medical image processing apparatuses each of which is equipped with the above-described innovative configuration, by referring to the accompanying drawings. Note that the same reference numbers are given for identical components in each figure, and duplicate description is omitted.

FIRST EMBODIMENT

By referring to FIG. 2 to FIG. 15, a description will be given of a case where the above-described configuration is applied to determination of a placement position of a lead-wire tip in a surgical operation of CRT.

(1) Configuration

Figure 2:
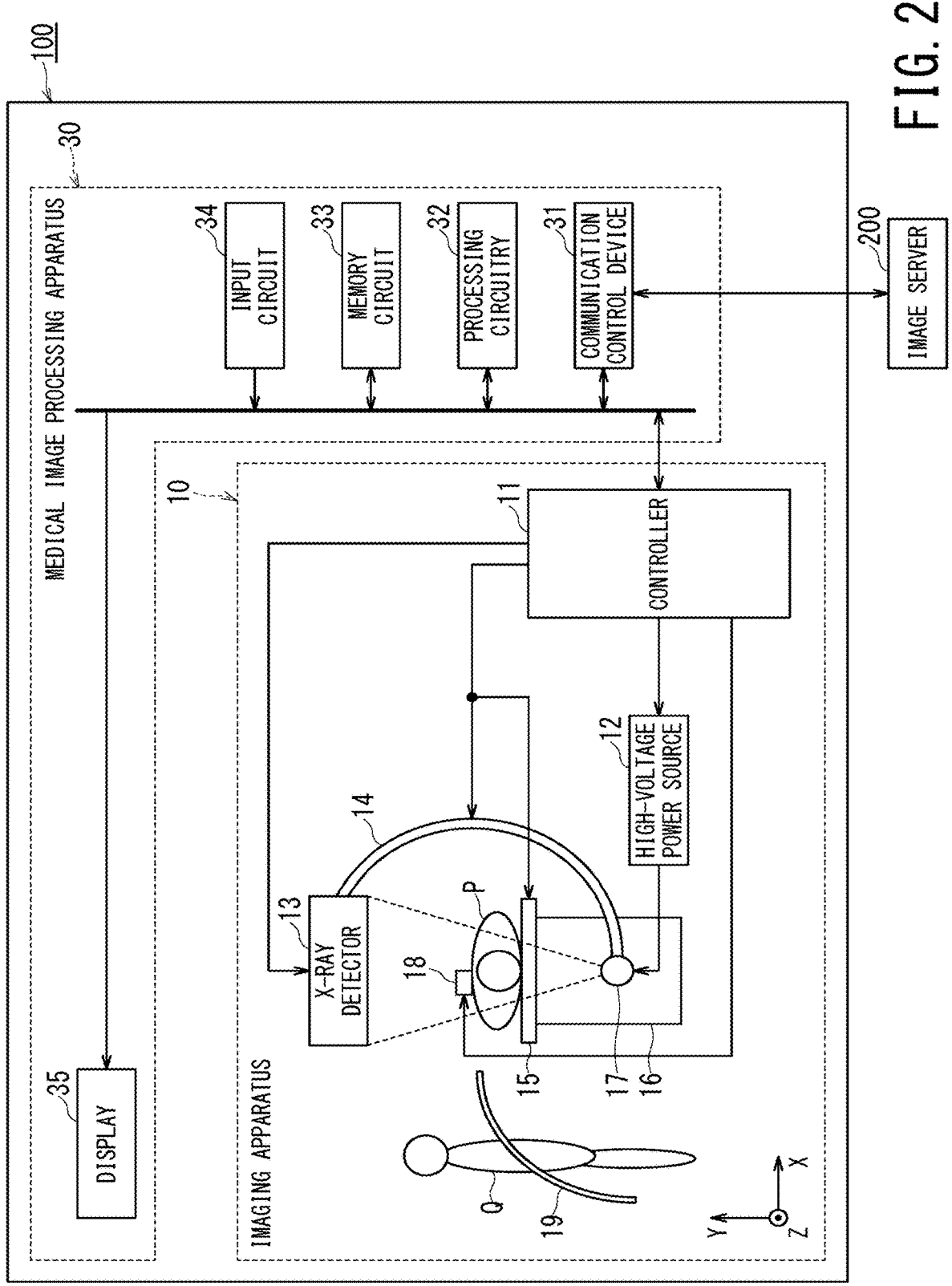
FIG. 2 is a conceptual configuration diagram illustrating a medical image diagnostic apparatus of the first embodiment.

FIG. 2 is a conceptual configuration diagram illustrating a medical image diagnostic apparatus of the first embodiment. The medical image diagnostic apparatus 100 shown in FIG. 2 includes an imaging apparatus 10 and a medical image processing apparatus 30.

As an example in FIG. 2, a description will be given of a case where the imaging apparatus 10 of the medical image diagnostic apparatus 100 is an X-ray fluoroscopic-imaging apparatus.

Note that the imaging apparatus 10 used for an interventional operation is not limited to an X-ray fluoroscopic-imaging apparatus. In an interventional operation, for instance, another modality such as an MRI (Magnetic Resonance Imaging) apparatus, an X-ray CT (Computed Tomography) apparatus, and an ultrasonic diagnostic apparatus is used for observing an object. Thus, the imaging apparatus 10 of the medical image diagnostic apparatus 10 is equipped with appropriate configuration depending on the type of the medical image diagnostic apparatus 10. For instance, in the case of an MRI apparatus, the medical image diagnostic apparatus 10 is equipped with configuration of acquiring magnetic resonance signals such as a static magnetic field magnet and a gradient coil.

The imaging apparatus 10 shown in FIG. 2 includes a controller 11, a high-voltage power source 12, an X-ray detector 13, a C-arm 14, a table 15, a bed 16, and an X-ray generator 17.

The controller 11 includes a non-illustrated processor such as a CPU (Central Processing Unit) and a memory. The controller 11 controls the high-voltage power source 12, the X-ray detector 13, the C-arm 14, the table 15, the bed 16, and the X-ray generator 17 so as to control the entire imaging operation.

The high-voltage power source 12 supplies the X-ray generator 17 with electric power necessary for irradiation of X-rays under the control of the controller 11.

The X-ray detector 13 is disposed at one end of the C-arm 14 so as to face the X-ray generator 17 disposed at the other end of the C-arm 14, in such a manner that the object P placed on the table 15 of the bed 16 is interposed between the X-ray detector 13 and the X-ray generator 17.

The X-ray detector 13 detects X-rays having passed through the object P with, e.g., many X-ray detection elements arrayed in a matrix pattern (not shown). X-rays detected by the X-ray detection elements are converted into electric signals and transmitted as medical image data to the medical image processing apparatus 30 via the controller 11.

In X-ray fluoroscopic imaging, medical images are acquired at respective time phases by a method called pulsed fluoroscopy in which an X-ray pulse is emitted from several times to several tens of times per second in order to suppress exposure in continuous imaging. Thus, medical images are time-sequentially acquired at predetermined time intervals in X-ray fluoroscopic imaging.

The X-ray detector 13 and the X-ray generator 17 are driven by the C-arm 14 under the control of the controller 11 such that the X-ray detector 13 and the X-ray generator 17 integrally rotate about the object P.

Although FIG. 1 shows a case where the X-ray generator 17 is supported by the C-arm 14 under the table 15 so as to be located on the floor side (i.e., an undertube type), this is only an example. The imaging apparatus 10 may be configured as an overtube type in which the X-ray generator 17 is supported by the C-arm 14 over the table 15 so as to be located on the ceiling side.

The bed 16 is installed on the floor surface, and supports the table 15. In FIG. 2, the Y-axis direction is the vertical direction. The table 15 horizontally moves within an X-Z plane which is perpendicular to the Y-axis and moves upward and downward in the Y-axis direction, under the control of the controller 11.

The X-ray generator 17 generates X-rays by using high voltage supplied from the high-voltage power source 12. X-rays generated by the X-ray generator 17 are radiated toward a target part of the object P. An irradiation adjustment mechanism is provided on the X-ray output side of the X-ray generator 17, and includes components such as an irradiation-field diaphragm equipped with plural lead blades and a compensation filter formed of, e.g., silicone rubber.

The biological information acquisition apparatus 18 is attached to the object P. The biological information acquisition apparatus 18 is configured of, e.g., an electrocardiograph and/or an ultrasonic diagnostic apparatus. When the biological information acquisition apparatus 18 is an electrocardiograph, biological information to be acquired is an electrocardiogram. An electrocardiogram includes at least two types which are a body-surface electrocardiogram and an intracardiac electrocardiogram. A body-surface electrocardiogram indicates overall cardiac systole action, and an intracardiac electrocardiogram indicates systole action of localized myocardium by measuring local potential with a catheter which is equipped with electrodes and inserted into a heart.

Additionally, when the biological information acquisition apparatus 18 is an ultrasonic diagnostic apparatus, biological information to be acquired is an ultrasonic diagnostic image. The ultrasonic diagnostic apparatus may be equipped with a transesophageal probe so that the transesophageal probe is inserted into inside of the body of the object P and a cardiac ultrasonic diagnostic image (i.e., so-called ultrasonic cardiogram) is acquired as biological information.

An operating surgeon Q inserts the treatment device 19 into inside of the body of the object P, and performs necessary treatment or procedure. The treatment device 19 in CRT is each lead-wire of a pacemaker. The operating surgeon Q inserts each lead-wire tip from a blood vessel of the object P into inside of the body by using a catheter, and places each lead-wire tip at an appropriate position in the heart.

The medical image processing apparatus 30 of the medical image diagnostic apparatus 100 shown in FIG. 2 includes a communication control device 31, processing circuitry 32, a memory circuit 33, an input circuit 34, and a display 35.

The control circuitry 32 is interconnected with respective hardware components constituting the medical image processing apparatus 30 via a bus as a transmission path of common signals. Note that the medical image processing apparatus 30 is equipped with a storage medium drive in some cases.

The communication control device 31 implements various types of communication protocols according to a network aspect. Here, an electronic network means the entire information communication network using telecommunications technology, and includes, e.g., a telephone communication network, an optical fiber communication network, a cable communication network, and a satellite communication network in addition to a hospital LAN (Local Area Network), a wireless/wired LAN, and the Internet network.

The medical image diagnostic apparatus 100 acquires previously acquired medical image data from an image server 200 via an electronic network. The previously acquired medical image data are, e.g., MR image data acquired by an MRI apparatus and CT image data acquired by an X-ray CT apparatus. The image server 200 may be configured as a system on a cloud.

The memory circuit 33 is configured of, e.g., a hard disc, an optical disc, and a semiconductor memory element such as a RAM (Random Access Memory) and a flash memory. The memory circuit 33 may be configured as a circuit to which a portable medium such as a USB (Universal Serial Bus) memory and a DVD (Digital Video Disk) is detachably connected. The memory circuit 33 stores image data and data necessary for executing programs such as an operating system in addition to various types of programs executed by the processing circuitry 32. Additionally, the memory circuit 33 may store a program of a GUI (Graphical User Interface) which enables input of various types of commands for controlling the operating system and input from the input circuit 34.

The input circuit 34 includes an input device such as a pointing device. The input circuit 34 outputs input-information inputted by an operator via the input device to the processing circuitry 32. The input device of the medical image diagnostic apparatus 100 may be equipped with a sight-line input system which can acquire, e.g., movement of the visual line of the operating surgeon Q as input information.

The display 35 is a display device such as a liquid crystal display panel, a plasma display panel, and an organic EL (Electro Luminescence) panel. The display 35 displays, e.g., a medical image and biological information under the control of the processing circuitry 32.

The processing circuitry 32 may be configured of a special-purpose hardware or be configured to implement various types of functions described below by software processing of its built-in processor. As an example here, a description will be given of a case where the processing circuitry 32 implements various types of functions by software processing of its processor.

The above-described processor means, e.g., a circuit such as a special-purpose or general-purpose CPU, a graphics processing unit (GPU), an application specific integrated circuit (ASIC), a programmable logic device, and a field programmable gate array (FPGA). The above-described programmable logic device includes, e.g., a simple programmable logic device (SPLD) and a complex programmable logic device (CPLD). The processing circuitry 32 implements various types of functions by reading out programs stored in the memory circuit 33 and executing the programs. Additionally or alternatively, the processing circuitry 32 implements various types of functions by reading out programs stored in its own processer and executing the programs.

Further, the processing circuitry 32 may be configured of a single processor or may be configured of a combination of plural processors which are independent of each other. In the latter case, plural memory circuits 33 may be provided for the respective processors so that programs executed by each processor are stored in the memory circuit 33 corresponding to this processor. As a further modification, one memory circuit 33 may collectively store all the programs corresponding to the respective functions of the plural processors.

Figure 3:
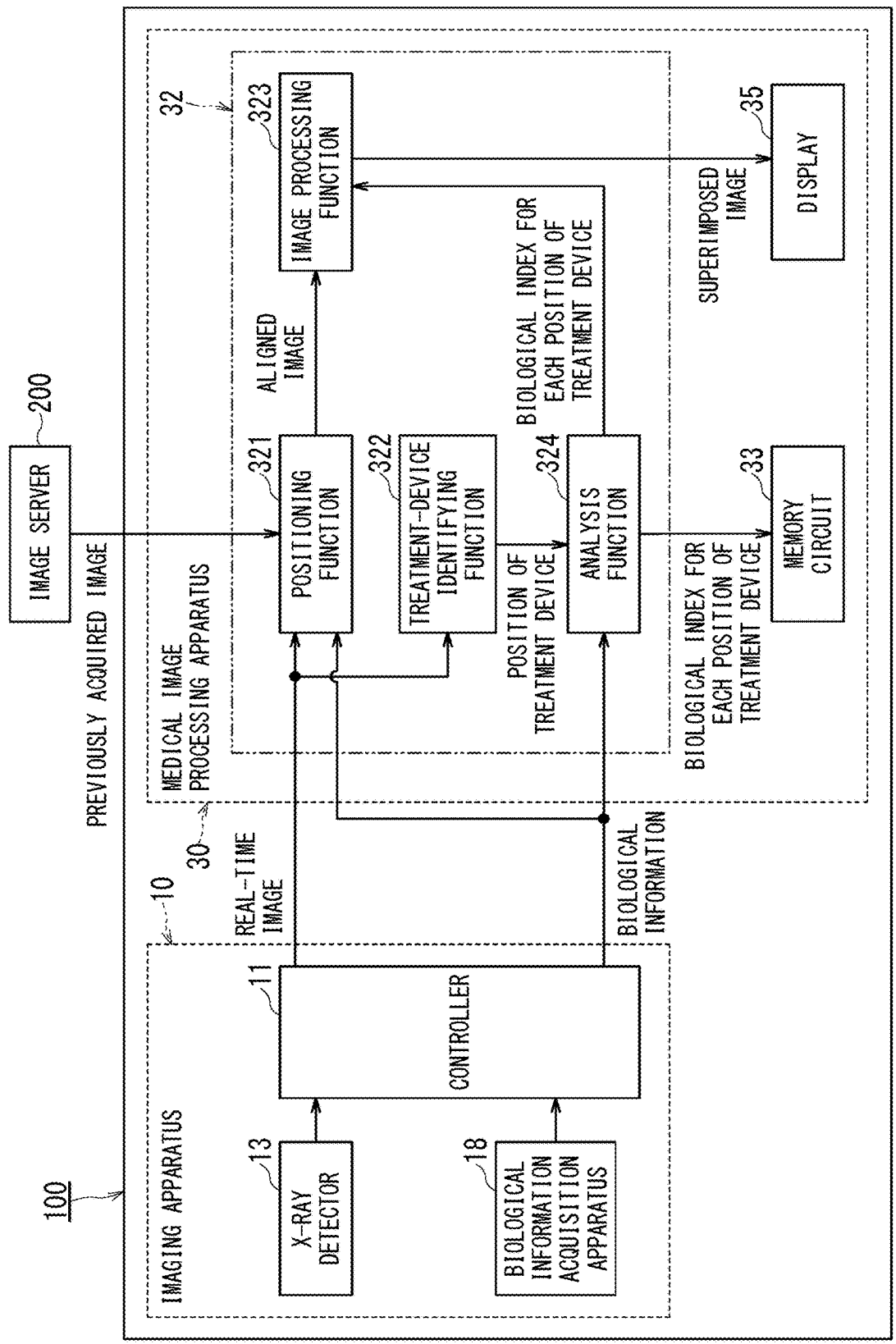
FIG. 3 is a functional block diagram illustrating detailed configuration of the medical image processing apparatus shown in FIG. 2.

FIG. 3 is a functional block diagram illustrating detailed configuration of the medical image processing apparatus 30 shown in FIG. 2. The processing circuitry 32 of the medical image processing apparatus 30 has a positioning function 321, a treatment-device identifying function 322, an image processing function 323, and an analysis function 324.

As an example here, it is defined that the first medical image means each of plural time-sequential medical images acquired from the same region of a certain object P by the imaging apparatus 10 on a real-time basis. Further, it is defined that the second medical image means each medical image previously acquired from the same imaging region of the same object P as the first medical image, and the above-described "previously" means to be in advance of acquiring the first medical image(s).

Hereinafter, the first medical image is referred to as a real-time image, and the second medical image is referred to as a previously acquired image.

The positioning function 321 performs positioning between a real-time image and a previously acquired image.

The positioning function 321 extracts anatomical features (e.g., anatomical landmarks and anatomically characteristic parts) from a real-time image and a previously acquired image, and performs positioning based on the extracted anatomical features. Anatomical features are extracted by, e.g., pattern matching. Pattern matching is a method of extracting respective anatomical features from a real-time image and a previously acquired image on the basis of template image data of a standard human model which include structural information such as shape of each organ, relative positional relationship between respective organs, arrangement of blood vessels, and relative positional relationship between respective blood vessels. Positioning is performed on the basis of anatomical features extracted by pattern matching.

Additionally, the positioning function 321 may use shading information of surrounding tissues such as a cardiac lumen and a backbone for positing between a real-time image and a previously acquired image. Since conventional techniques can be used for positional processing, a detailed description of positional processing is omitted.

The treatment-device identifying function 32 detects a position of a tip of a treatment device from a real-time image. Additionally, the treatment-device identifying function 322 extracts moving trace of a tip of a treatment device by automatically tracking (tracing) the tip of the treatment device. The position of the tip of the treatment device may be detected by, e.g., a positional sensor mounted on the treatment device or pattern matching on the basis of characteristic shape of the tip of the treatment device in a manner similar to the extraction method of anatomical features.

Additionally, in some cases, the treatment device 19 is equipped with a radio-opaque marker on its tip such that the treatment device 19 can be observed in X-ray fluoroscopic imaging. Since the marker is radio-opaque, a part corresponding the marker in an X-ray fluoroscopic image is depicted as a pixel region where X-ray transmission amount is smaller than its surrounding region. Thus, for instance, in the case of an X-ray fluoroscopic image in which a region with larger X-ray transmission amount such as an air region in a lung is more brightly depicted, the marker is darkly depicted as a pixel region where each pixel value is low.

Hence, by identifying such a part indicative of the marker by image processing, it is possible to depict the position of the treatment device 19 and/or the moving trace of the treatment device 19. Since conventional techniques can be used for a method of acquiring the position of the treatment device 19, its detailed description is omitted.

The image processing function 323 generates such an image that a biological index is superimposed on a medical image, depending on movement of the position of the treatment device 19. As to an image on which a biological index generated by the image processing function 323 is added, it will be described below.

The analysis function 324 computes a biological index by analyzing biological information acquired from the object P. Biological information is acquired together with acquisition of each medical image, and the analysis function 324 computes a biological index indicative of treatment degree for each of plural time phase on the basis of the acquired biological information. Biological information acquired in the case of CRT is an electrocardiogram or a cardiac ultrasonic image. The analysis method of biological information performed by the analysis function 324 will be described below.

The memory circuit 33 stores each biological index computed by the analysis function 324 and the position of the treatment device 19 identified by the treatment-device identifying function 322 for each medical image from which biological information corresponding to the biological index is acquired, in such a manner that each biological index and the corresponding position of the treatment device 19 are associated with each other.

(2) Operation

Figure 4:
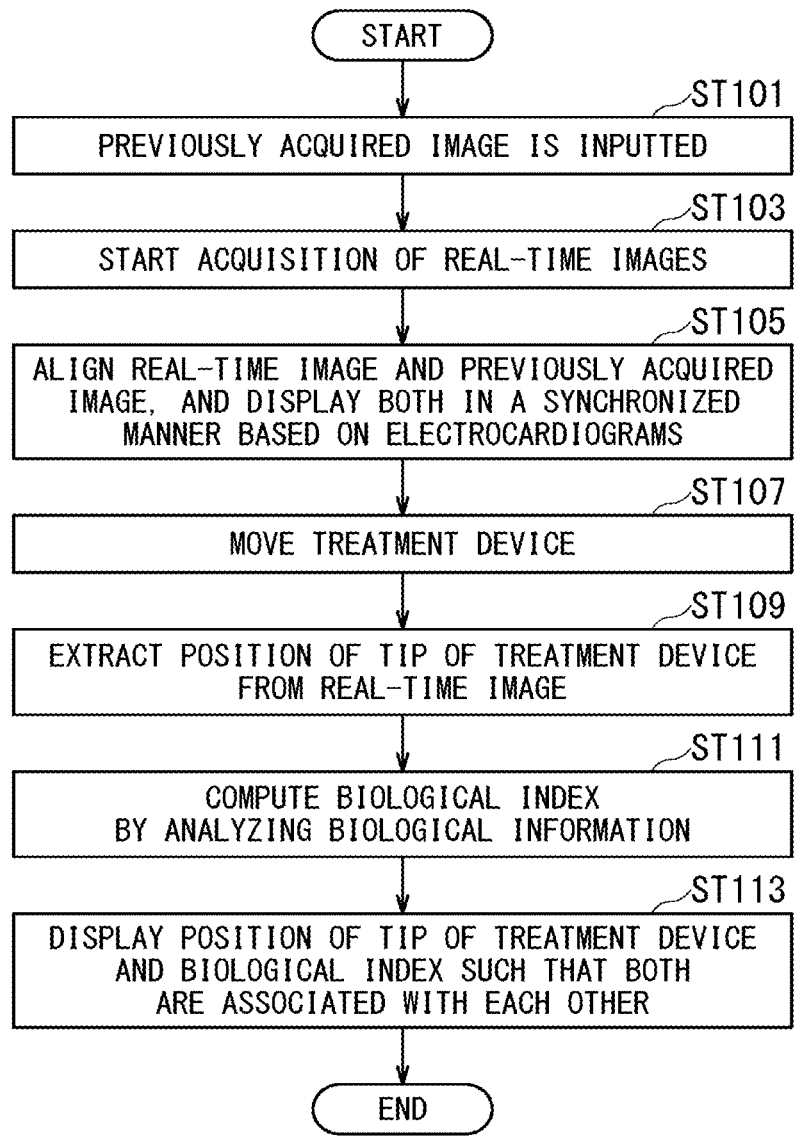
FIG. 4 is a flowchart illustrating processing of the medical image diagnostic apparatus to be performed during an interventional operation.

FIG. 4 is a flowchart illustrating processing of the medical image diagnostic apparatus 100 to be performed during an interventional operation. In the following, according to the step numbers in the flowchart shown in FIG. 4, processing of the medical image diagnostic apparatus 100 of the first embodiment will be described by referring to FIG. 5 to FIG. 7 as required.

In the step ST101, data of at least one previously acquired image are inputted from the image server 200 to the medical image processing apparatus 30 of the medical image diagnostic apparatus 100.

In the next step ST103, the imaging apparatus 10 of the medical image diagnostic apparatus 100 starts an imaging operation, i.e., acquisition of real-time images.

In the next step ST105, the positioning function 321 performs positioning between each real-time image and the previously acquired image. Further, the positioning function 321 causes the display 35 to display the previously acquired image and each real-time image such that both are synchronized with each other in terms of cardiac time phase on the basis of time-sequentially acquired electrocardiograms as described below.

The positioning function 321 performs positioning between each real-time image and the previously acquired image based on anatomical features. As described above, anatomical features are extracted by pattern matching on the basis of template image data of a standard human body. These template image data may be previously stored in the memory circuit 33 of the medical image diagnostic apparatus 100, and the term "previously" means to be in advance of start of imaging, e.g., from the time of installation and adjustment of the medical image diagnostic apparatus 100. Additionally or alternatively, these template image data may be acquired from the image server 200 as needed.

By extracting anatomical landmarks from each real-time image and the previously acquired image through pattern matching, anatomically characteristic parts such as an atrium, a ventricle, a coronary vein, an aorta, an aortic valve, and a mitral valve are identified. Positioning between each real-time image and the previously acquired image is performed on the basis of these anatomically characteristic parts.

As an example here, each real-time image acquired by the imaging apparatus 10 which is an X-ray fluoroscopic-imaging apparatus is a two-dimensional image. The previously acquired image acquired by an MRI apparatus or an X-ray CT apparatus is a three-dimensional image.

In positioning (i.e., alignment) between a real-time image which is a two-dimensional image and a previously acquired image which is a three-dimensional image, first, a two-dimensional image is generated from the three-dimensional image by an image processing method called mean intensity projection. Mean intensity projection is a method of determining each pixel value of an image, which is obtained by projecting three-dimensional image data on a projection plane in the same direction as the X-ray irradiation direction at the time of imaging a real-time image, on the basis of an average value of respective voxel values of the corresponding voxels arranged along the X-ray irradiation direction in the three-dimensional image data.

A two-dimensional image generated from three-dimensional image by mean intensity projection has the same projection plane as that of each real-time image. Thus, it is possible to align a real-time image and a previously acquired image by extracting anatomical landmarks from each of the real-time image which is a two-dimensional image and a two-dimensional image generated from the three-dimensional image of the previously acquired image.

Although a description has been given of the case where the imaging apparatus 10 is an X-ray fluoroscopic-imaging apparatus of a single plane type equipped with one C-arm 14 and acquires two-dimensional real-time image, this is only one aspect. The imaging apparatus 10 may be configured as an X-ray fluoroscopic-imaging apparatus of a biplane type equipped with two arms. In the case of an X-ray fluoroscopic-imaging apparatus of a biplane type, three-dimensional image can be generated by performing X-ray fluoroscopic imaging in two directions at the same time. In this manner, three-dimensional images can be generated by an X-ray fluoroscopic-imaging apparatus and it is also possible to perform positioning between each real-time image and a previously acquired image both of which are three-dimensional images.

Further, an electrocardiogram may be simultaneously acquired at the time of acquiring each previously acquired image. In other words, data of each previously acquired image may be four-dimensional image data which include an electrocardiogram as accompanying information of the three-dimensional image data.

The positioning function 321 synchronizes each real-time image, which is acquired together with an electrocardiogram, with the previously acquired image, which was acquired together with an electrocardiogram, in terms of cardiac time phase.

Hereinafter, the processing of the step ST105 in FIG. 4 will be described in detail by referring to FIG. 5 and FIG. 6.

Figure 5:
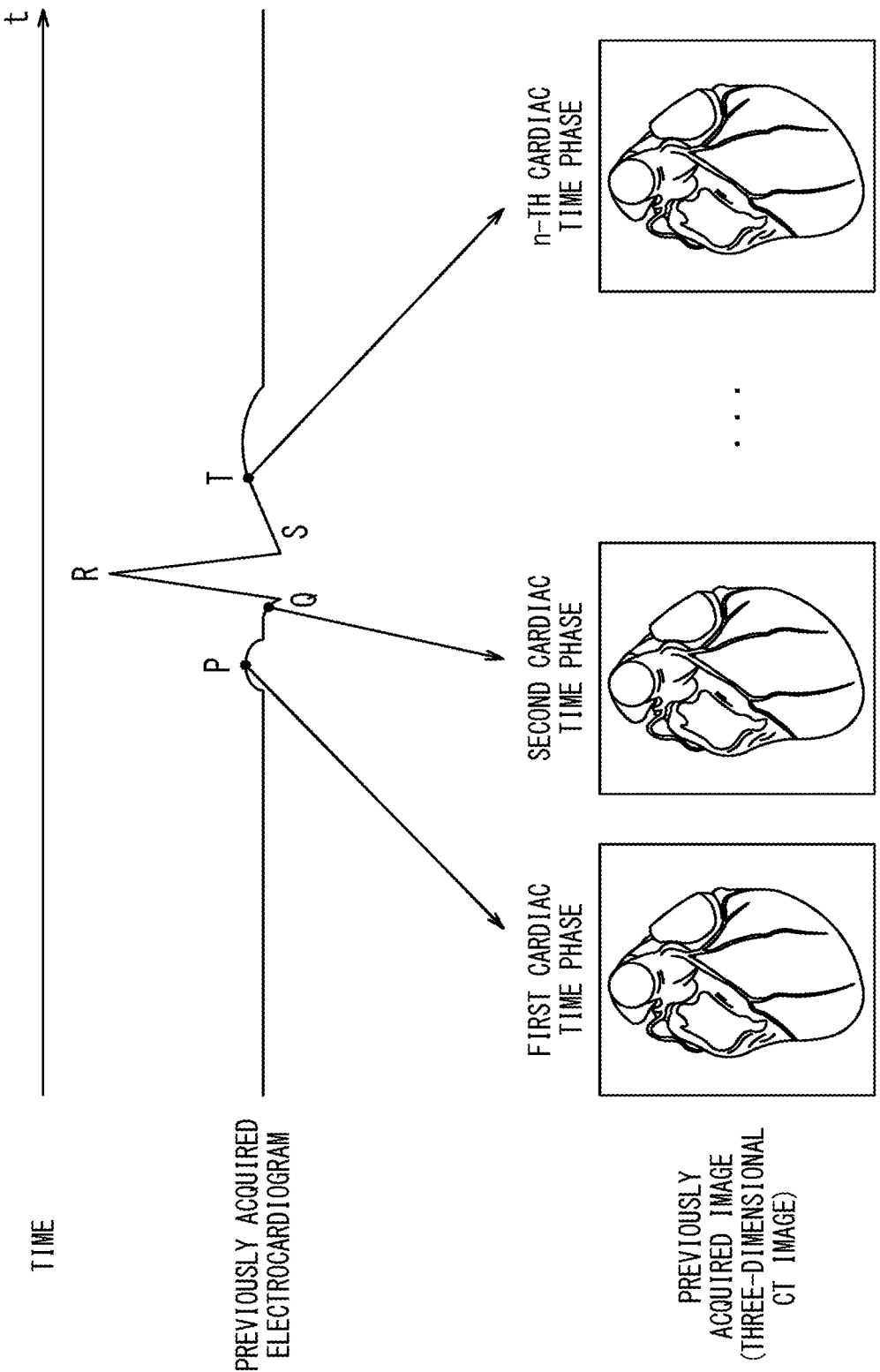
FIG. 5 is a schematic diagram illustrating a previously acquired image which is acquired as four-dimensional image data.

FIG. 5 is a schematic diagram illustrating previously acquired images which are four-dimensional image data. Data of previously acquired image are four-dimensional image data composed of an electrocardiogram and three-dimensional image. In FIG. 5, the top part indicates a temporal axis, the middle part indicates a previously acquired electrocardiogram, and the bottom part indicates three-dimensional CT images which are previously acquired images.

The previously acquired electrocardiogram shown in FIG. 5 indicates characteristic waveforms of a P-wave, a Q-wave, an R-wave, an S-wave, and a T-wave. Additionally, it is shown that the three-dimensional CT image (i.e., the previously acquired image in FIG. 5) includes respective images of plural cardiac time phases which include the first cardiac time phase, the second cardiac time phase, . . . and the n-th cardiac time phase A cardiac time phase is identified on the basis of, e.g., a P-wave, a Q-wave, an R-wave, an S-wave, and a T-wave which are characteristic wave forms constituting an electrocardiogram. FIG. 5 illustrates a case where the three-dimensional CT image at the first cardiac time phase belongs to the cardiac time phase of the P-wave, the three-dimensional CT image at the second cardiac time phase belongs to the cardiac time phase of the Q-wave, and the three-dimensional CT image at the n-th cardiac time phase belongs to the cardiac time phase of the T-wave.

As described above, three-dimensional CT image data are image data whose cardiac time phase is identified on the basis of a previously acquired electrocardiogram. An electrocardiogram is also measured at the time of acquiring each real-time image. In X-ray fluoroscopic imaging, medical images are time-sequentially acquired at predetermined time intervals by pulsed fluoroscopy. The positioning function 321 can identify a cardiac time phase for each medical image to be continuously acquired at predetermined time intervals. The positioning function 321 extracts the previously acquired image whose cardiac time phase is the same as the current cardiac time phase of the object P identified from each electrocardiogram to be measured in real time, superimposes the extracted previously acquired image on the updated real-time image of the object P, and causes the display 35 to display the real-time image on which the extracted previously acquired image is superimposed. This processing is repeated such that display on the display 35 is sequentially updated.

Figure 6:
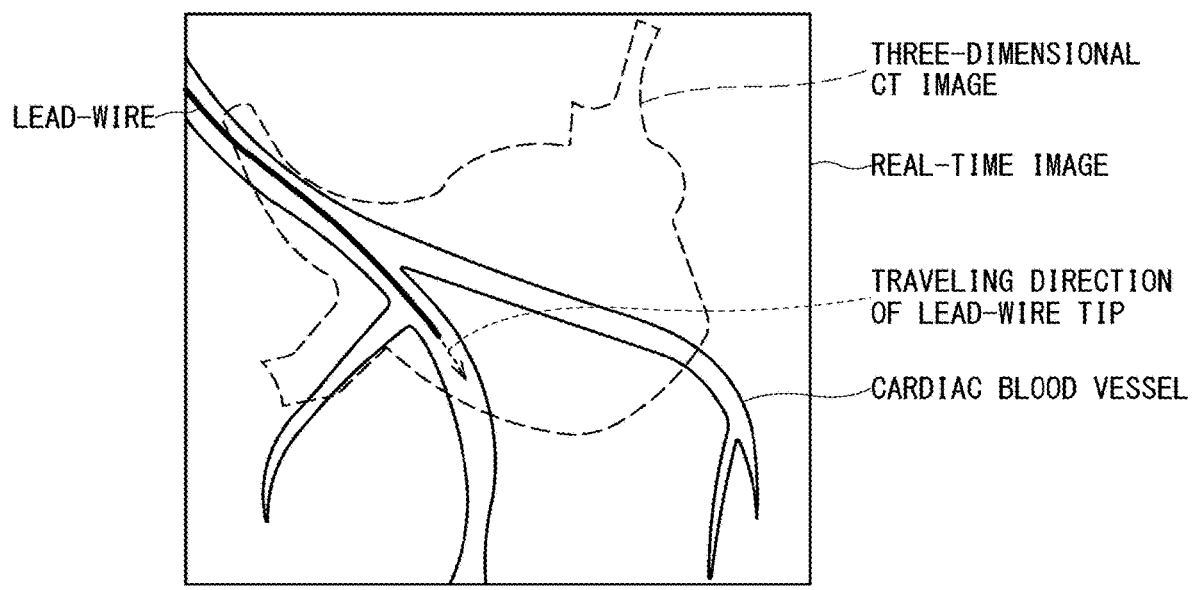
FIG. 6 is a schematic diagram illustrating superimposed display of a previously acquired image and a real-time image.

FIG. 6 is a schematic diagram illustrating superimposed display of a previously acquired image and a real-time image. In FIG. 6, a real-time image is indicated by solid lines, and a three-dimensional CT image which is a previously acquired image is indicated by broken lines. FIG. 6 illustrates a two-dimensional real-time image on which a three-dimensional CT image is superimposed by the above-described mean intensity projection. Note that the real-time image and the three-dimensional CT image are aligned with each other by the above-described method.

In a real-time image acquired by X-ray fluoroscopic imaging, it is possible to depict a structure with low degree of X-ray transmission such as a bone, a contrast-enhanced vessel, and the treatment device 19. The image shown in FIG. 6 depicts contrast-enhanced cardiac vessels and the lead-wire which is the treatment device 19.

It is difficult to accurately extract anatomical structures such as myocardium and a vascular wall from a real-time image. Contrastively, a previously acquired image acquired by an X-ray CT apparatus is an image in which anatomical structures are clearly depicted. As shown in FIG. 6, it is possible to supplement information on anatomical structures in the real-time image by superimposing an anatomical contour depicted in the three-dimensional CT image which is a previously acquired image.

Although a description has been given of the case where a contour of a three-dimensional CT image is displayed on a real-time image in FIG. 6, the present embodiment is not limited to the aspect of FIG. 6. For instance, transparent degree may be set on a three-dimensional CT image sterically generated by volume rendering processing so that this three-dimensional CT image is transparently superimposed on a real-time image to be displayed. Additionally, it is possible to acquire information by analyzing the three-dimensional CT image such as vascular calcification and vascular thickening so that the acquired information is distinguishably superimposed and displayed on a three-dimensional CT image by using (chromatic) colors and/or figures.

Returning to FIG. 4, the description of the flowchart is continued.

In the next step ST107, the operating surgeon Q operates the catheter inserted into inside of a blood vessel, and moves the tip of the treatment device 19. FIG. 6 shows a case where the lead-wire tip is the treatment device 19 in CRT and the lead-wire tip moves in the direction indicated by the broken-line arrow.

In the next step ST109, the treatment-device identifying function 322 identifies the position of the lead-wire tip, which is the treatment device 19, from each real-time image. The position of the lead-wire tip may be identified by, e.g., template matching on the basis of the characteristic shape of the lead-wire tip or be identified on the basis of change in pixel value between respective real-time images.

In the next step ST111, the analysis function 324 computes biological indexes by analyzing biological information. For instance, when the biological information acquisition apparatus 18 is an electrocardiograph, electrocardiograms are acquired as biological information. The analysis function 324 computes biological indexes, each of which indicate degree of a treatment effect, by analyzing electrocardiograms.

Figure 7:
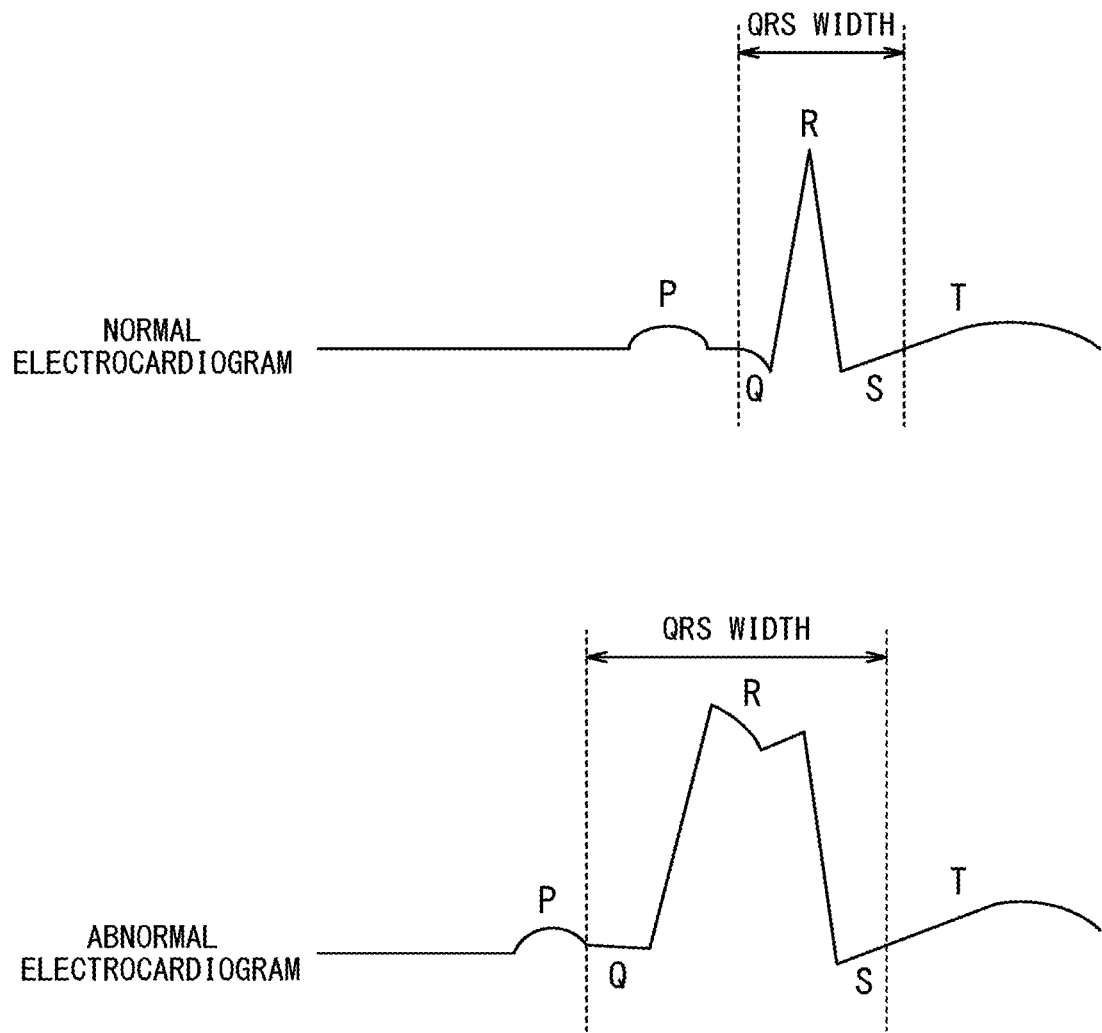
FIG. 7 is a schematic diagram illustrating computation method of a biological index on the basis of electrocardiograms.

FIG. 7 is a schematic diagram illustrating computation method of each biological index on the basis of electrocardiograms. The upper part of FIG. 7 schematically illustrates a normal electrocardiogram, and the lower part of FIG. 7 schematically illustrates an abnormal electrocardiogram. In each of the electrocardiograms, QRS width is indicated by a broken line and QRS width means width from the start of the Q-wave to the end of the S-wave. QRS width in an abnormal electrocardiogram is wider than that in a normal electrocardiogram.

In a normal heart, ventricles and atria sequentially contract so that blood is pumped. For instance, when systole of ventricles and atria fall into an asynchronous state in terms of systole, the heart cannot appropriately pump blood. Such abnormality in systole appears as prolongation of QRS width in an electrocardiogram. Thus, this QRS width is an index for determining a treatment effect in CRT.

In CRT, electric current outputted from each lead-wire tip influences systole of myocardium, and thus a treatment effect is expected. Hence, by analyzing change in QRS width in electrocardiograms acquired from the object P during an interventional operation, it is possible to compute degree of the treatment effect of electric current outputted from each lead-wire tip on systole of myocardium in an asynchronous state for each position of each lead-wire tip.

The analysis function 324 computes QRS width as a biological index indicative of the treatment effect for each position of the lead-wire tip by analyzing electrocardiograms acquired from the electrocardiograph. The QRS width computed by the analysis function 324 is transmitted to the image processing function 323 and displayed on the display 35 in such an aspect that the QRS width is associated with the position of each lead-wire tip. Additionally, the QRS width computed by the analysis function 324 may be stored in the memory circuit 33 in such a manner that the stored QRS width is associated with the corresponding position of each lead-wire tip.

Returning to FIG. 4, the description of the flowchart is continued.

In the next step ST113, the image processing function 323 causes the display 35 to display the position of each lead-wire tip and the QRS width which is computed as a biological index by the analysis function 324, in such a manner that both are associated with each other. The display 35 may display the position of each lead-wire tip and the biological index associated with the position of each lead-wire tip on each real-time image in which the position of each lead-wire tip is extracted. Additionally or alternatively, the display 35 may display the position of each lead-wire tip and the biological index associated with the position of each lead-wire tip on an arbitrary real-time image. For instance, the display 35 may display a biological index, which is associated with the position of each lead-wire tip computed over plural time phases, on one arbitrary real-time image.

After acquiring the previously acquired image from the image server 200 in the step ST101, the medical image processing apparatus 30 sequentially repeats the processing from the step ST103 to the step ST113 by the number of real-time images. In other words, each time a real-time image to be time-sequentially imaged is inputted to the medical image processing apparatus 30 on a real-time basis, the updated real-time image and the previously acquired image are aligned with each other and are synchronized with each other in terms of cardiac time phase so as to be displayed in the step ST105, and the position of each tip of the treatment device 19 and a biological index are computed and distinguishably displayed in the steps ST107 to ST113.

Note that the treatment-device identifying function 322 can detect movement of the treatment device 19 and the processing from the step ST107 to the step ST113 in FIG. 4 may be repeated each time the treatment device 19 moves.

In this manner, the medical image processing apparatus 30 sequentially updates assistance information such as (a) each real-time image and the previously acquired image to be displayed together on the display 35 in a superimposed manner and (b) each biological index and the position of each tip of the treatment device 19 to be displayed together with those real-time image and previously acquired image. Accordingly, the operating surgeon Q can appropriately continue an interventional operation while observing or referring to such assistance information.

The foregoing is the description of the flowchart of FIG. 4.

Hereinafter, by referring to respective schematic diagrams of FIG. 8 to FIG. 11, a description will be given of some display aspects in which the image processing function 323 causes the display 35 to display the position of each lead-wire tip and the biological index computed by the analysis function 324 such that both are associated with each other.

Figure 8:
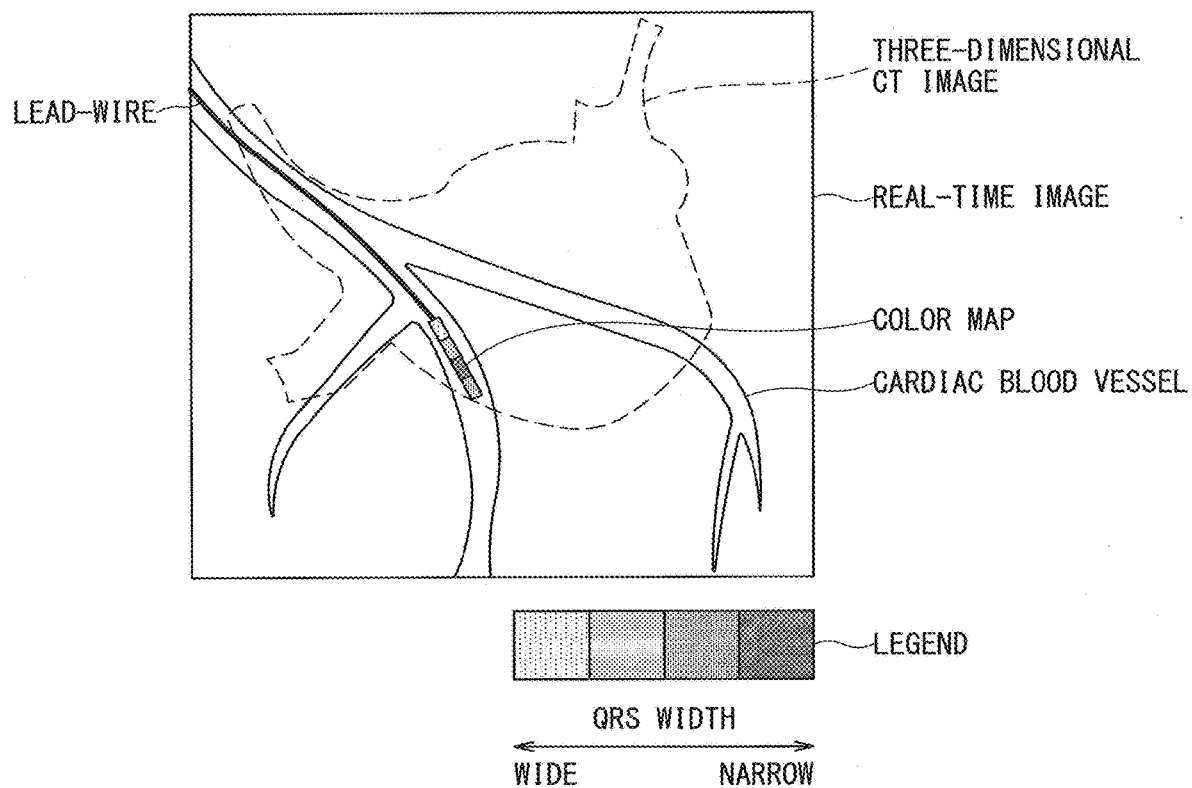
FIG. 8 is a schematic diagram illustrating a display aspect of a biological index at a position of a lead-wire tip by using a color map.

FIG. 8 is a schematic diagram illustrating display of a biological index at the position of the lead-wire tip by using a color map. FIG. 8 illustrates a color map which is generated on the basis of biological indexes and is superimposed and displayed on the real-time image shown in FIG. 6. FIG. 8 shows the real-time image which is displayed in accordance with the legend on its bottom part. A color map is, e.g., a display aspect in which a color in accordance with QRS width is computed for each position of the lead-wire tip and is assigned to the pixel corresponding to this position of the lead-wire tip.

In the color map shown in FIG. 8, QRS width is distinguished by grayscale for simplicity in such a manner that a pixel with narrower QRS width is more darkly (i.e., more blackly) depicted. A distinguishable display aspect of QRS width is not limited to grayscale but chromatic colors such as red, blue, and green may be assigned as a distinguishable display aspect in accordance with QRS width.

Each region of the color map may have predetermined area centering on the position of the lead-wire tip.

QRS width is computed for each position of the lead-wire tip. In FIG. 8, each time the position of the lead-wire tip moves, QRS width at the updated position is computed, and the color map is updated in accordance with the trace of the lead-wire tip (i.e., the longer the trace becomes, the larger the area of the color map in the image becomes).

However, a display aspect of a color map is not limited to the aspect of FIG. 8. For instance, QRS width may be computed at predetermined time intervals each time the position of lead-wire tip is moved by a predetermined distance so that the updated color map is superimposed and displayed on the updated moving trace of the lead-wire tip.

Additionally, a color corresponding to QRS width may be displayed only on the pixel(s) corresponding to the current position of the lead-wire tip. For instance, when QRS width becomes narrower as the lead-wire tip is moved, the color of the pixel corresponding to the lead-wire tip may become gradually darker each time the color map is updated.

Since change in QRS width is displayed as a color map in accordance with movement of the position of the lead-wire tip as shown in FIG. 8, the operating surgeon Q can intuitively understand change in QRS width for each position of the lead-wire tip and can easily determine the appropriate placement position of lead-wire tip.

Figure 9:
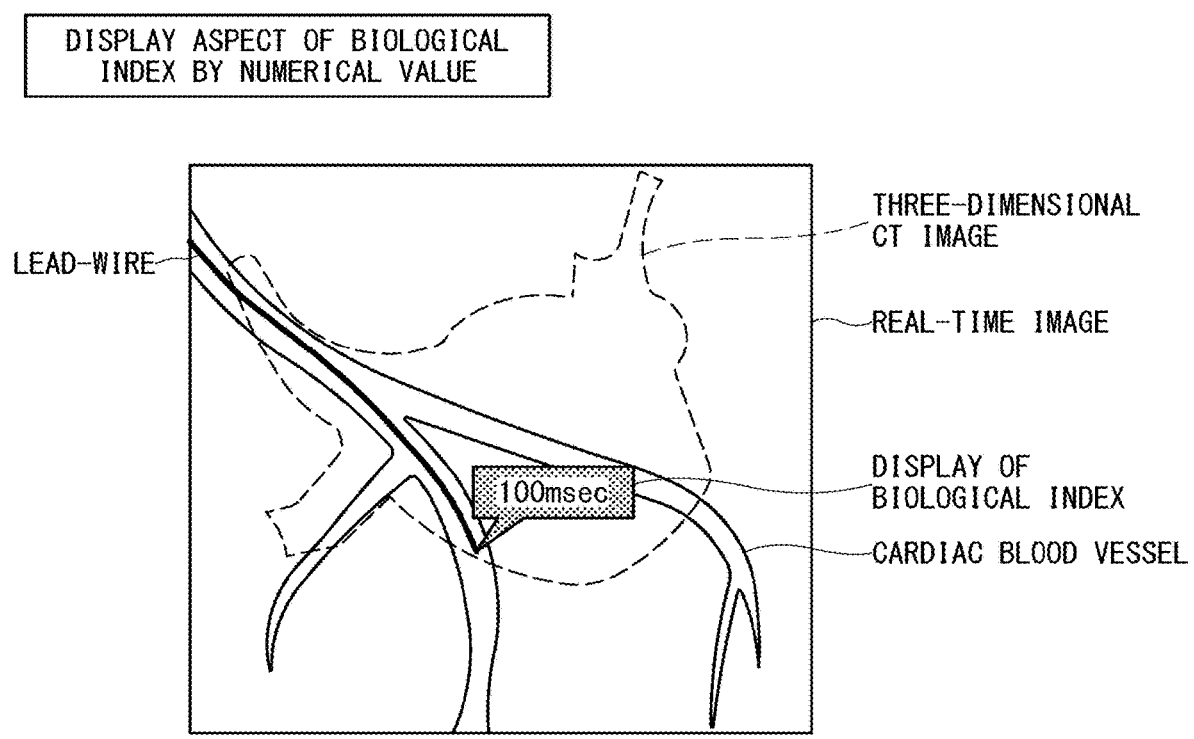
FIG. 9 is a schematic diagram illustrating another display aspect of a biological index in which the biological index at the position of the lead-wire tip is indicated by a numerical value.

FIG. 9 is a schematic diagram illustrating another display aspect of a biological index in which the biological index at the position of the lead-wire tip is indicated by a numerical value. FIG. 9 differs from FIG. 8 in that QRS width is indicated by a numerical value at the position of the lead-wire tip. In FIG. 9, a balloon-type frame is indicated at the position of the lead-wire tip, and the numerical value of QRS width is displayed inside this balloon-type frame. In the case of FIG. 9, QRS width computed at the position of the lead-wire tip is 100 msec ("msec" means millisecond).

The numerical value of QRS width at the position of the lead-wire tip in FIG. 9 may be updated and displayed so as to follow the current position of the lead-wire tip during movement of the lead-wire tip. In this case, when the position of the lead-wire tip is moved, QRS width is updated and changed and the numerical value is also updated and changed so as to match the updated QRS width on a real-time basis.

Display of QRS width by a numerical value is not limited to the aspect of FIG. 9. For instance, it is possible to display the QRS width at the position selected via the input circuit 34. The memory circuit 33 stores QRS width such that each QRS width is associated with the corresponding position of the lead-wire tip. For instance, respective components of the medical image diagnostic apparatus 100 may be configured such that movement of the visual line of operating surgeon Q is detected to select the position corresponding to the current visual line on the real-time image and QRS width at the selected position is displayed at the selected position on the real-time image.

By causing the memory circuit 33 to store each QRS width in the state of being associated with the corresponding position of the lead-wire tip as described above, it is possible to confirm QRS width at the position which the lead-wire tip has passed through, without moving the lead-wire tip back to this position again.

Additionally, as to the balloon-type figure in which the numerical value of QRS width is displayed in FIG. 9, this balloon-type figure may be displayed by a chromatic color or an achromatic color which changes in a stepwise fashion depending on QRS width as descried in FIG. 8. By displaying such distinguishable color together with the numerical value of QRS width, it is possible for the operating surgeon Q to intuitively determine the appropriate placement position of the lead-wire tip on the basis of the specific numerical value.

Figure 10:
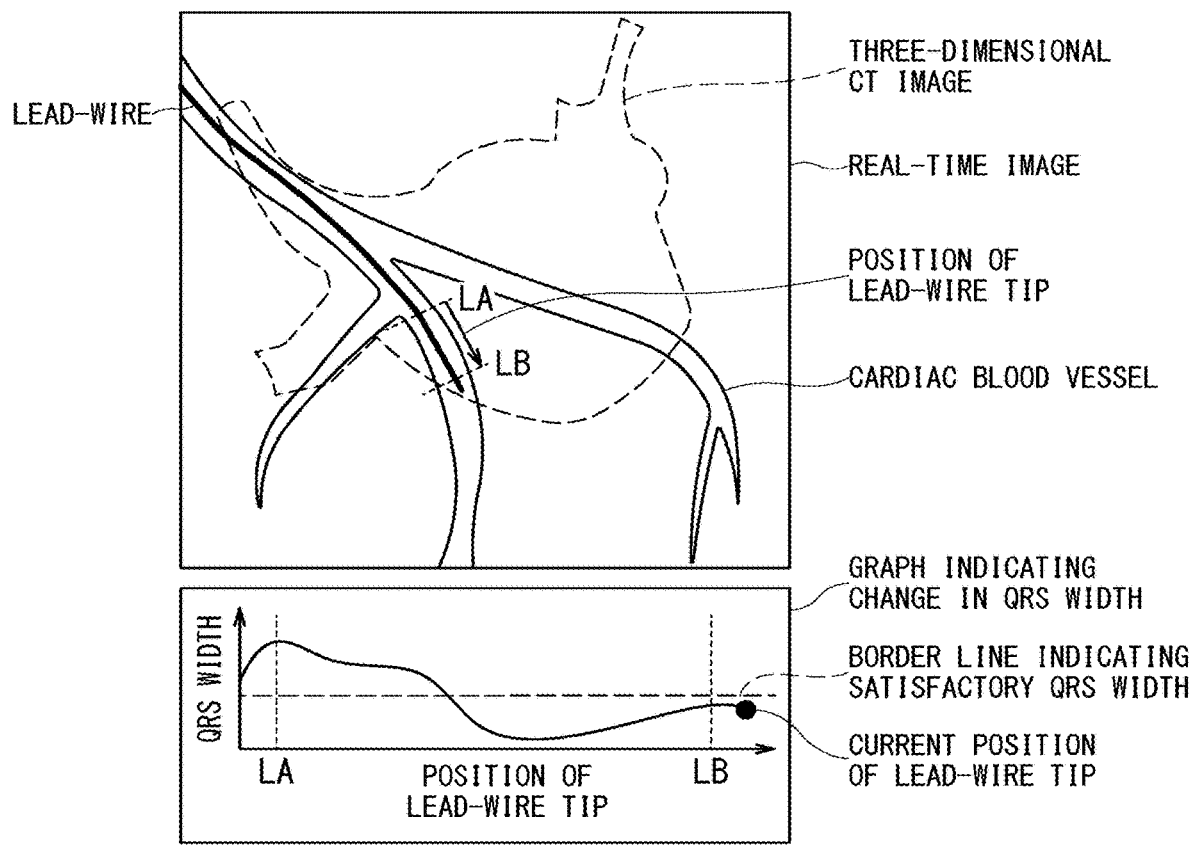
FIG. 10 is a schematic diagram illustrating still another display aspect of a biological index which includes a graph of QRS width for each position of the lead-wire tip.

FIG. 10 is a schematic diagram illustrating still another display aspect of a biological index which includes a graph of QRS width for each position of the lead-wire tip. In the graph shown at the bottom part of FIG. 10, the horizontal axis indicates a position of the lead-wire tip and the vertical axis indicates QRS width at each position of the lead-wire tip. FIG. 10 differs from FIG. 8 and FIG. 9 in that change in QRS width between respective positions of the lead-wire tip is indicated by a curved line.

The upper part of FIG. 10 shows the real-time image, and the lower part of FIG. 10 shows the graph indicative of change in QRS width when the lead-wire tip moved from the region indicated by the broken line LA to the region indicated by the broken line LB. In the graph shown in the lower part of FIG. 10, the border line indicative of satisfactory QRS width is indicated by the straight broken-line in parallel with the horizontal axis. When the lead-wire tip is placed at a position where QRS width is narrower than the width indicated by this border line, a satisfactory treatment can be expected.

Additionally, on the curve line of the graph in the lower part of FIG. 10, a blackly-filled circle is superimposed as a mark indicative of the current position of the lead-wire tip. The respective components of the medical image diagnostic apparatus 100 may be configured such that this circular mark moves on the curve line of the graph so as to follow the current position of lead-wire tip in accordance with movement of the lead-wire tip.

Note that the mark indicative of the current position of the lead-wire tip is not limited to the circle mark but other marks such as a triangle may be used. Additionally, it is not necessarily required to superimpose and display the mark indicative of the current position of the lead-wire tip on the curve line of the graph. For instance, in the graph, the region of the background corresponding to the position of the lead-wire tip may be displayed by a color different from colors of other regions so that the difference in color indicates correspondence relationship between the position of the lead-wire tip and QRS width.

Additionally, the position of the lead-wire tip corresponding to the curve line selected via the input circuit 34 may be displayed on the real-time image by, e.g., a sign or symbol.

Further, the graph shown in the lower part of FIG. 10 may be updated each time the position of the lead-wire tip is moved and QRS width is newly computed. In other words, the respective components of the medical image diagnostic apparatus 100 may be configured such that the curved line is prolonged each time QRS width is computed for the updated position of the lead-wire tip in accordance with movement of the lead-wire tip.

The operating surgeon Q can intuitively determine the appropriate placement position of the lead-wire tip by observing the biological index on the graph described with FIG. 10. Since the operating surgeon Q can compare respective positions in terms of numerical value of QRS width before determining a placement position of the lead-wire tip, the operating surgeon Q can accurately judge an appropriate placement position of the lead-wire tip.

As to QRS width which is a biological index indicative of a treatment effect, a description has been given of cases where QRS width is displayed in an intuitively distinguishable manner with the use of, e.g., a color map and/or a graph in FIG. 8 to FIG. 10. The operating surgeon Q can easily determine the appropriate placement position of the lead-wire tip on the basis of display by a color map and/or a graph.

As to a display aspect of wideness or narrowness of QRS width which is a biological index indicative of a treatment effect in the medical image diagnostic apparatus 100, it is not limited to the aspect describes in FIG. 8 to FIG. 10.

Figure 11:
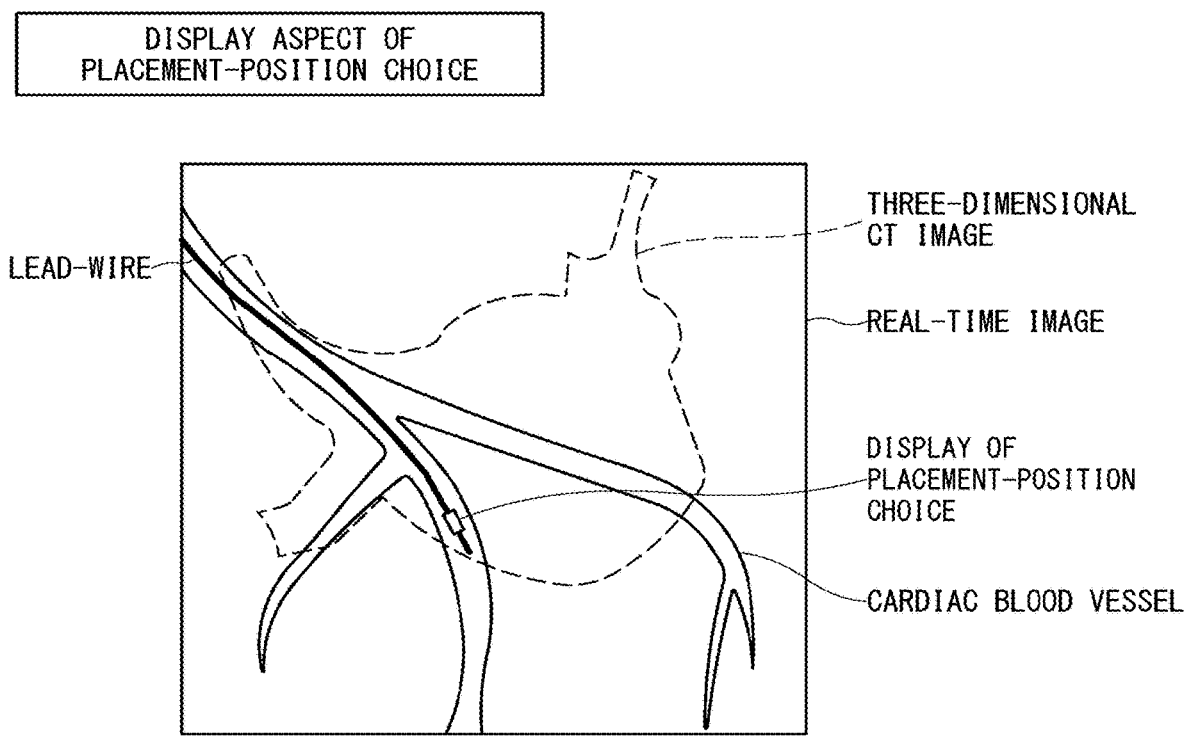
FIG. 11 is a schematic diagram illustrating display of a placement-position choice for the lead-wire tip.

The respective components of the medical image diagnostic apparatus 100 may be configured such that the analysis function 324 computes at least one choice for the placement-position based on QRS width, which is a biological index indicative of a treatment effect, and the image processing function 323 causes the display 35 to superimpose and display the computed placement-position choice on each real-time image FIG. 11 is a schematic diagram illustrating display of a placement-position choice for the lead-wire tip. FIG. 11 differs from FIG. 6 in that a mark indicative of the placement-position choice for the lead-wire tip is displayed on the real-time image. As shown in FIG. 11, a white rectangle surrounded by a black frame is indicated at the placement-position choice for the lead-wire tip.

As described in FIG. 4, the medical image processing apparatus 30 sequentially updates assistance information such as (a) each real-time image and the previously acquired image to be displayed together on the display 35 in a superimposed manner and (b) each biological index and the position of each lead-wire tip to be displayed together with those real-time image and previously acquired image. For this reason, the placement-position choice for the lead-wire tip may be updated on a real-time basis in accordance with movement of the position of the lead-wire tip.

Specifically, for instance, the medical image diagnostic apparatus 100 repeats processing of measuring QRS width at the position of the lead-wire tip and storing the measured QRS width each time the operating surgeon Q moves the position of one lead-wire tip. Further, each time the lead-wire is moved, the medical image diagnostic apparatus 100 repeats processing of selecting the position with the minimum QRS width from all the positions where QRS width is measured on the movement trace of the tip of this one lead-wire including the current position of this lead-wire tip. The medical image diagnostic apparatus 100 causes the display 35 to update the placement-position choice such that the selected position with the minimum QRS width is displayed as the placement-position choice on a real-time basis.

Although a description has been given of the case where one figure is displayed as a placement-position choice for a tip of one lead-wire in FIG. 11, plural placement-position choices may be displayed for a tip of one lead-wire. For instance, the analysis function 324 may compute the position where QRS width is equal to or smaller than a predetermined threshold value, as the placement-position choice for the lead-wire tip. This predetermined threshold value is a border value indicative of a satisfactory QRS width. When placement-position choices for respective tips of plural lead-wires are computed on the basis of such a determination condition, all the computed placement-position choices may be displayed or the placement-position choice closest to the current position of the lead-wire tip may be displayed.

Additionally, the display aspects of FIG. 8 to FIG. 10 and the display aspect of FIG. 11 may be used in combination. For instance, the respective components of the medical image diagnostic apparatus 100 may be configured such that the current position of lead-wire tip is displayed by the color corresponding to the QRS width at this current position and the placement-position choice is simultaneously displayed.

The placement-position choice may be computed on the basis of a previously acquired image and/or intracardiac electrocardiograms previously acquired by an electrophysiological examination. The analysis function 324 can compute a biological index on the basis of a previously acquired image and/or biological information such as a previously acquired intracardiac electrocardiogram. After narrowing down appropriate placement positions of the lead-wire tip in accordance with the previously computed placement-position choice in this manner, the placement position of the lead-wire tip may be determined on the basis of a biological index which is computed in real time and displayed at the current position of the lead-wire tip.

Although a description has been given of the case where a previously acquired image is superimposed on a real-time image in FIG. 8 to FIG. 11, each real-time image and the previously acquired image may be separately displayed. For instance, each real-time image and the previously acquired image may be displayed in parallel.

Further, though a description has been given of the case where assistance information such as a color map and a placement-position choice is superimposed on a real-time image in FIG. 8 to FIG. 11, the image on which such assistance information is superimposed is not limited to a real-time image. For instance, a color map and/or a placement-position choice may be superimposed and displayed on a previously acquired image. Additionally, a color map and/or a placement-position choice may be superimposed and displayed on one of a real-time image and a previously acquired image or may be superimposed and displayed on both of a real-time image and a previously acquired image. Hereinafter, a description will be given of a case where a biological index is superimposed and displayed on a previously acquired image by referring to FIG. 12 to FIG. 15.

Figure 12:
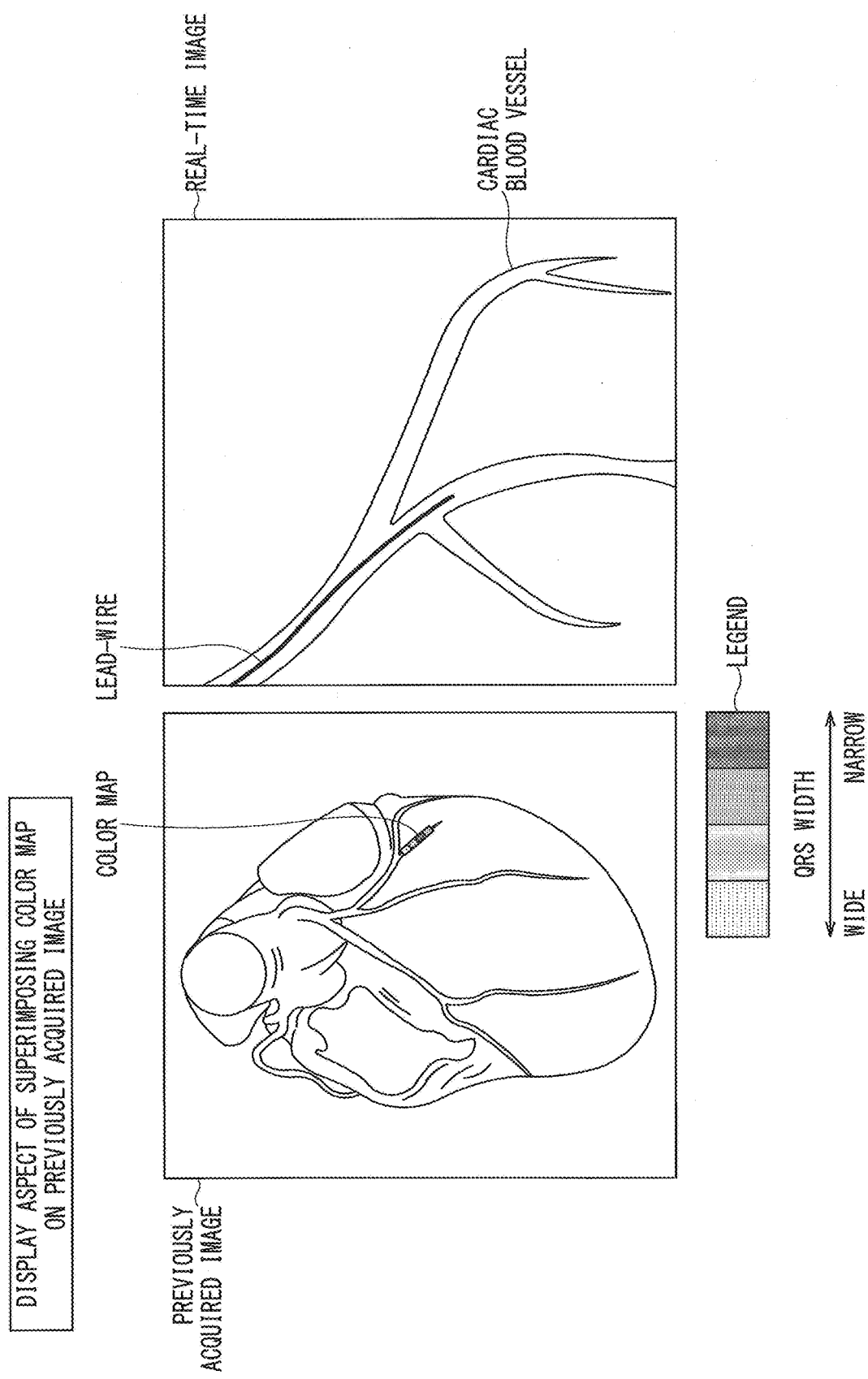
FIG. 12 is a schematic diagram illustrating one display aspect in which a color map is superimposed and displayed on a previously acquired image.

FIG. 12 is a schematic diagram illustrating one display aspect in which a color map is superimposed and displayed on a previously acquired image. The left side of FIG. 12 is a previously acquired image, and the right side of FIG. 12 is a real-time image. In FIG. 12, the previously acquired image is a three-dimensional image generated by performing volume rendering processing on three-dimensional image data. When data of a three-dimensional image are four-dimensional image data including an electrocardiogram, a moving image in synchronization with the cardiac time phase of the object P may be displayed.

The previously acquired image and the real-time image are aligned with each other by the positioning function 321. The color map is displayed along the trace of the lead-wire tip in a manner similar to FIG. 8. In other words, on the previously acquired image, the color map is superimposed and displayed at the position that matches the position of the lead-wire tip on the real-time image.

In FIG. 12, QRS width is distinguished by grayscale for simplicity in such a manner that a pixel with narrower QRS width is more darkly depicted in a manner similar to FIG. 8. Note that a distinguishable display aspect of QRS width is not limited to grayscale but chromatic colors such as red, blue, and green may be assigned as a distinguishable display aspect in accordance with QRS width. Additionally, each region of the color map may have predetermined area centering on the position of the lead-wire tip. As to the distinguishable display of QRS width in a color map, the same holds true for FIG. 13.

Although the color map is superimposed and displayed only on the previously acquired image in the case of FIG. 12, the color map may be superimposed and displayed on both of the previously acquired image and the real-time image. Additionally, though a three-dimensional image is displayed as the previously acquired image in the case of FIG. 12, the display aspect of the previously acquired image is not limited to a three-dimensional image. For instance, the previously acquired image may be a curved MPR (Multi Planer Reconstruction) image (i.e., a CPR image).

Figure 13:
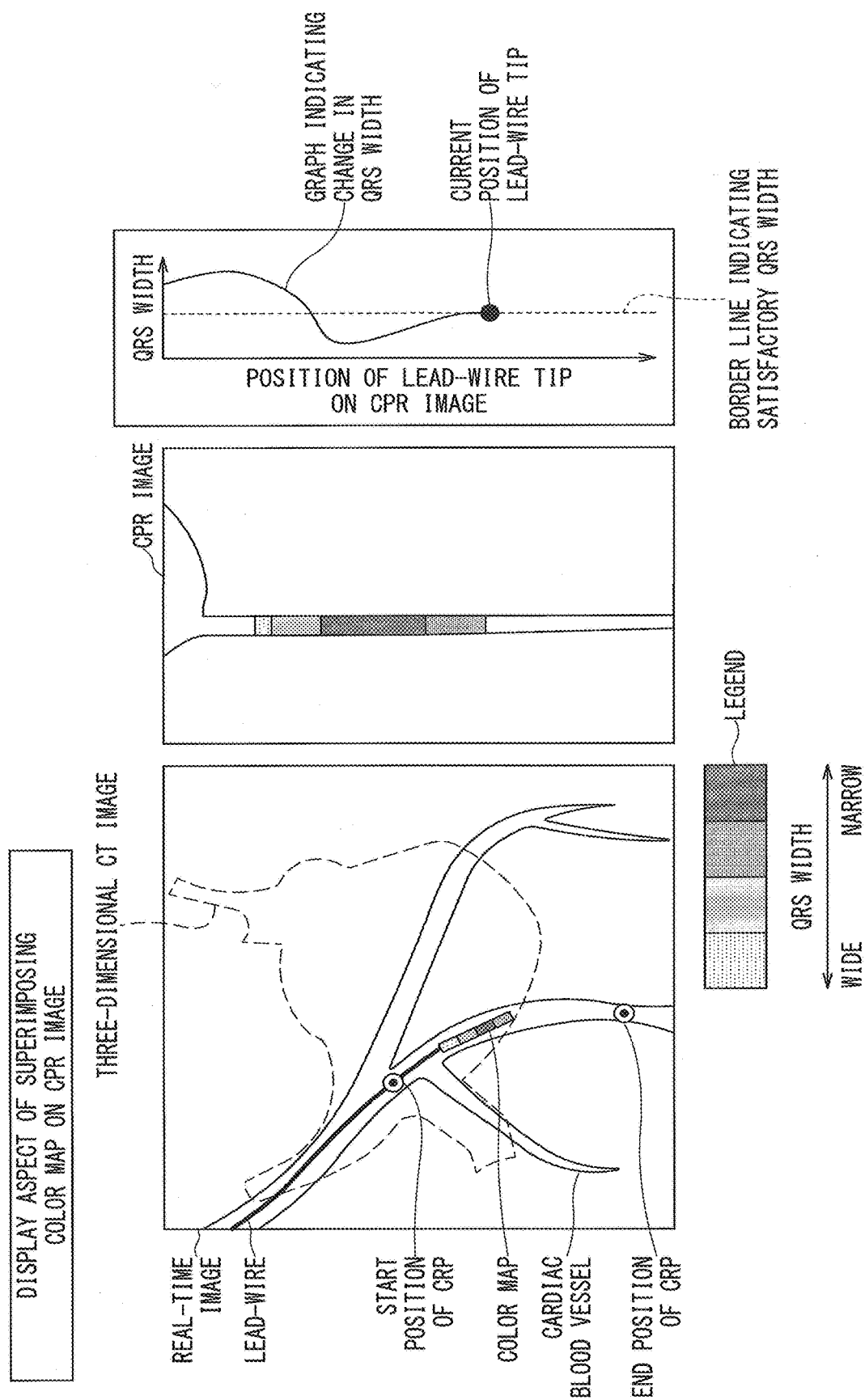
FIG. 13 is a schematic diagram illustrating one display aspect in which a color map is superimposed and displayed on a CPR image.

FIG. 13 is a schematic diagram illustrating one display aspect in which a color map is superimposed and displayed on a CPR image. The left side of FIG. 13 is a real-time image, the middle part of FIG. 13 is a CPR image. The right side of FIG. 13 is a graph in which the horizontal axis indicates a position of the lead-wire tip in the CPR image and the vertical axis indicates QRS width for each position of the lead-wire tip. FIG. 13 shows one display aspect in which the color map is superimposed and displayed on both of the CPR image and the real-time image. The CPR image is generated by performing CPR processing (i.e., curved MPR processing) on three-dimensional image data.

The CPR processing is image processing in which a tubular structure such as a three-dimensionally curved vessel is developed on a two-dimensional plane. A vascular CPR image is an image of a vascular cross-section on a two-dimensional plane in the case of crossing a blood vessel along its central line. Thus, in a CPR image, it is possible to observe volume change along a traveling direction of a blood vessel.

In the CPR processing, a CPR start position and a CPR end position are determined on a three-dimensional image in order to specify the blood vessel of a processing target. In the case of FIG. 13, CPR processing is performed under the premise that the target is the blood vessel into which the lead-wire is inserted at the present moment. The CPR start position is set to the branching position of the blood vessel into which the lead-wire is inserted, and the CPR end position is set to the downstream side of this blood vessel in FIG. 13, the respective two positions corresponding to the CPR start position and the CPR end position are displayed as circular marks on the real-time image.

The CPR image in FIG. 13 is an image of blood vessel data developed on a two-dimensional plane, which blood vessel data are included in three-dimensional image data and correspond to the blood vessel existing from the CPR start position to the CPR end position in the real-time image. Thus, the top edge of the CPR image in FIG. 13 matches the CPR start position in the real-time image, and the lower end matches the CPR end position of the real-time image.

On the CPR image shown in FIG. 13, the same color map as that displayed on the real-time image is superimposed and displayed. In other words, the moving trace of the lead-wire tip of the color map displayed on the CPR image is the same as that of the color map displayed on the real-time image. Change in QRS width for each position of the lead-wire tip in the CPR image is also indicated in the graph of FIG. 13.

Although a description has been given of the case where the same color map as the color map displayed on the real-time image is displayed on the CPR image in FIG. 13, the color map displayed on the CPR image and the color map displayed on the real-time image may be different from each other. For instance, the processing circuitry 32 may cause the display 35 to display the color map for a part of the moving trace of the lead-wire tip on the real-time image and to display the color map for the entire moving trace of the lead-wire tip on the CPR image.

Although a description has been given of the case where a biological index on the basis of QRS width is displayed as a color map in FIG. 8 and FIG. 13, a biological index is not limited to QRS width. A biological index may be computed on the basis of electric potential and/or amplitude of an electrocardiogram in a specific cardiac time phase.

Specifically, electric potential and/or amplitude of a specific waveform such as a Q-wave and/or a P-wave maybe compared with (or subtracted from) electric potential and/or amplitude in its normal waveform so that the difference between both is computed as a biological index. In this manner, the respective components of the medical image diagnostic apparatus 100 may be configured such that a biological index is computed for each cardiac time phase and a color map for each cardiac time phase is displayed on a CPR image. Additionally, the medical image diagnostic apparatus 100 may be configured such that a CPR image to be displayed can be switched for each specific cardiac time phase. Further, the medical image diagnostic apparatus 100 may be configured such that a moving picture of a CPR image for each cardiac time phase can be displayed by sequentially and continuously displaying CPR images for respective cardiac time phases in synchronization with the cardiac time phase of the object.

Moreover, when plural biological indexes are computed for the same position of the lead-wire tip, a color map maybe generated by performing statistical processing such as integration procedure, averaging procedure, median-value computation, maximum value computation, and minimum value computation. Further, statistical processing may be performed on biological indexes computed from electrocardiograms acquired in a predetermined period or be performed on biological indexes computed for a predetermined range of the entire moving trace of the lead-wire tip. Furthermore, the respective components of the medical image diagnostic apparatus 100 maybe configured such that a user can set a range to which statistical processing is applied.

In FIG. 12 and FIG. 13, a description has been given of the case where a previously acquired image and a real-time image are displayed in parallel. When a previously acquired image and a real-time image are displayed in parallel, both medical images may be different in time phase from each other. Additionally, respective biological indexes different from each other may be superimposed on both medical images.

As described above, information displayed on the display 35 is composed of combination of a medical image and assistance information. The assistance information is displayed together with a medical image such as a previously acquired image and a real-time image, and includes a medical image and/or a biological index for compensating morphological information. A biological index is displayed in a display form such as a color map and a numerical value. Additionally, biological indexes are subjected to statistical processing for a predetermined period and/or within a predetermined range in various ways. Further, since biological indexes are time-sequentially computed, display of a color map and/or a numerical value is performed by a moving picture or a still image. Display aspects of medical images include display forms and image types such as a still image, a moving image, a CPR image, and a rendering image. In other words, information displayed on the display 35 is composed of combination of respective factors related to display aspects of assistance information and combination of respective factors related to display aspects of medical images.

For instance, as to whether images of an observation target is displayed as a moving picture or a still image on the display 35, it may be arbitrarily selected and switched by a user. Specifically, in the case of displaying cardiac medical images as a moving picture synchronized with heartbeat, by further displaying change in biological index such as QRS width in synchronization with heartbeat, identification of the treatment position becomes easier than displaying the same content by still images. Additionally, by selecting a combination in which cerebral medical images are displayed by still images and biological indexes of different time phases are displayed as a moving picture, it facilitates to visually understand a treatment effect. By appropriately using display aspects in combination as described above, it is possible to display information in such a manner that a user can visually recognize assistance information more easily.

Although a description has been given of the case where a color map on the basis of a biological index is displayed on a previously acquired image in FIG. 12 and FIG. 13, a placement-position choice may be superimposed and displayed on a previously acquired image. Additionally, though a placement-position choice is determined without limiting an analysis period of biological indexes in FIG. 11, the analysis function 324 may determine a placement-position choice in a predetermined analysis period.

Figure 14:
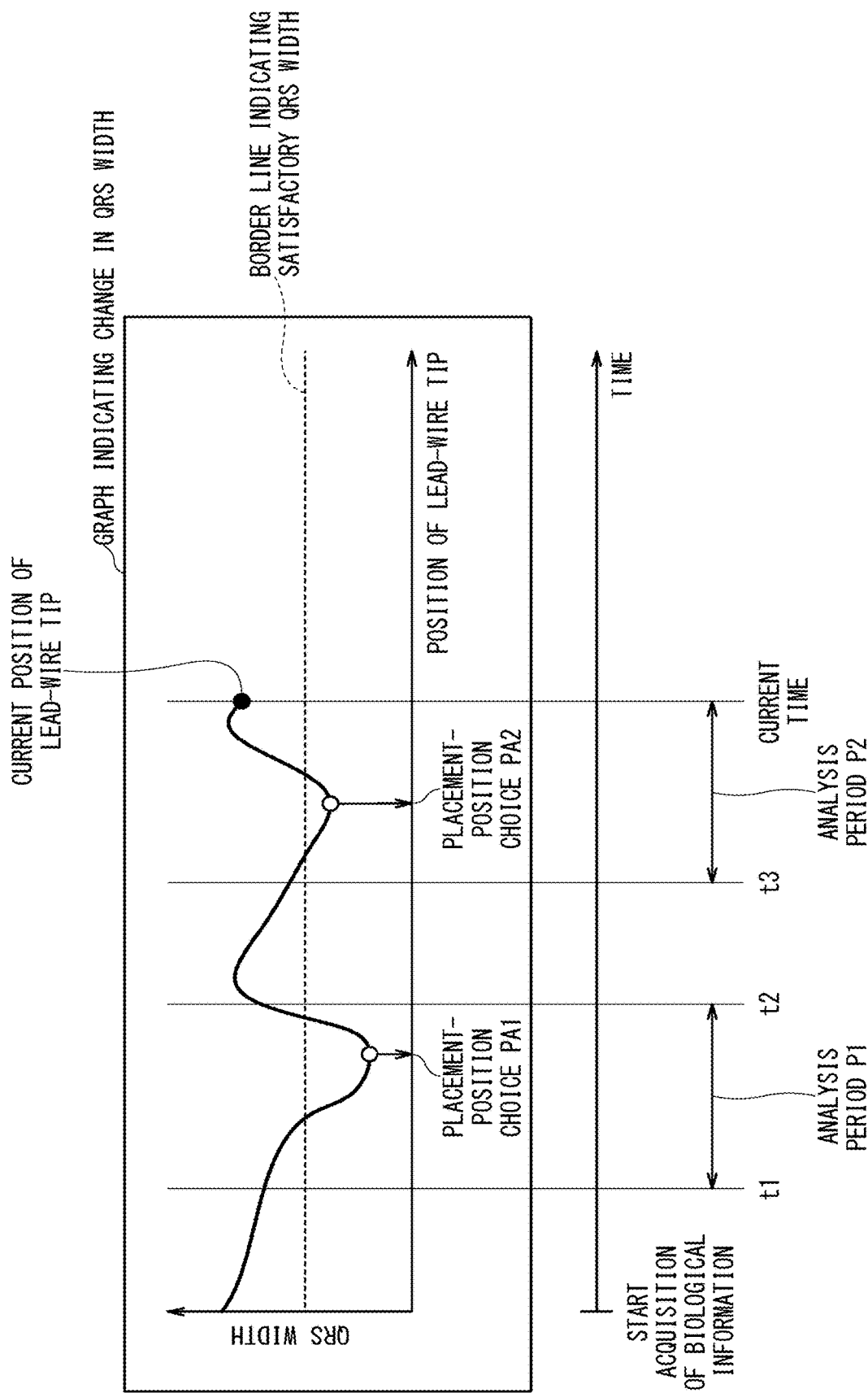
FIG. 14 is a timing chart illustrating an acquisition period of biological information and an analysis period of a placement-position choice.

FIG. 14 is a timing chart illustrating an acquisition period of biological information and each analysis period of a placement-position choice. The upper part of FIG. 14 is a graph in which the horizontal axis indicates a position of the lead-wire tip and the vertical axis indicates QRS width for each position of the lead-wire tip, and the horizontal axis below this graph in FIG. 14 indicates elapsed time from start of acquisition of electrocardiograms which are biological information. In the graph of FIG. 14, the position indicated by the black circle mark is the current position of the lead-wire tip.

FIG. 14 illustrates a case where each predetermined analysis period is a part of the entire period from start of acquisition of electrocardiograms to the current time. FIG. 14 illustrates a case where the analysis period P1 is set as a predetermined analysis period which does not include the current time, and the analysis period P2 is set as another predetermined analysis period which includes the current time. The analysis period P1 is the period between t1 and t2, and the analysis period P2 is the period from t3 to the current time. For instance, when the placement-position choice is determined as the position of the lead-wire tip where QRS width within the analysis period is the minimum, the placement-position choice in the analysis period P1 is the placement-position choice PA1. The placement-position choice PA1 is the position of the lead-wire tip where QRS width within the analysis period between t1 and t2 is the minimum value. Similarly, the placement-position choice in the analysis period P2 is the placement-position choice PA2, and this placement-position choice PA2 is the position of the lead-wire tip where QRS width within the analysis period from t3 to the current time is the minimum value.

Note that a determination condition of a placement-position choice is not limited to the minimum value of QRS width within an analysis period. For instance, a placement-position choice may be determined as the position of the lead-wire tip where QRS width is equal to or smaller than a predetermined threshold value, and this predetermined threshold value is the same as described above.

Figure 15:
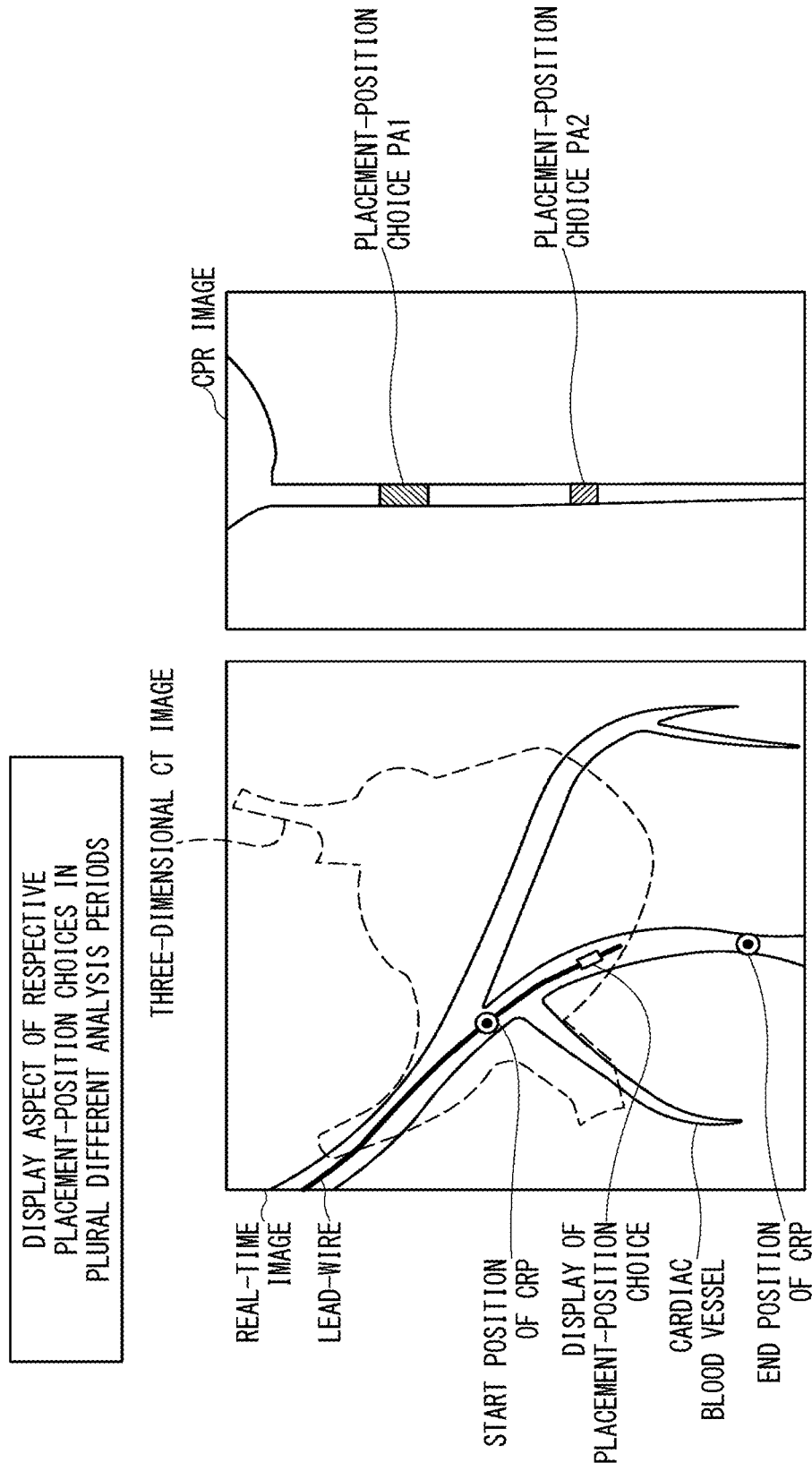
FIG. 15 is a schematic diagram illustrating a display aspect in which respective placement-position choices determined for plural different analysis periods are displayed on a previously acquired image and a real-time image.

FIG. 15 is a schematic diagram illustrating a display aspect in which respective placement-position choices determined for plural different analysis periods are displayed on a previously acquired image and a real-time image. The left part of FIG. 15 is a real-time image, and the right part of FIG. 15 is a CPR image. In the real-time image, only one placement-position choice PA2 is displayed and this placement-position choice PA2 is acquired in the analysis period P2 which includes the current position of the lead-wire tip. In the CPR image, both of the placement-position choice PA1 in the analysis period P1 and the placement-position choice PA2 in the analysis period P2 are displayed.

Note that the placement-position choice (s) acquired without limiting an analysis period may be displayed on the CPR image. In other words, the placement-position choice (s) acquired by setting the analysis period as the entire period from start of acquisition of biological information to the current time may be displayed on the CPR image. In this manner, biological indexes may be analyzed in plural different periods so that respective placement-position choices determined for the plural different periods are displayed on a real-time image and a previously acquired image.

According to the medical image diagnostic apparatus 100 of the first embodiment as described above, QRS width is computed for each position of the lead-wire tip from each electrocardiogram acquired on a real-time basis, and the computed QRS width is displayed in a distinguishable manner such as a color map. Thus, the operating surgeon Q can instantly judge the optimal placement position. Additionally, since change in QRS width for each position of the lead-wire tip can be intuitively recognized from, e.g., a color map and a graph, the optimal placement position can be easily determined. Further, by displaying the placement-position choice (s), it is possible to assist the operating surgeon Q in determining the optimal placement position. Hence, determination of the placement position is facilitated by performing display in which the position of the lead-wire tip and biological information are associated with each other, which contributes to reduction in surgery time.

SECOND EMBODIMENT

In the first embodiment, a description has been given of the case where electrocardiograms are acquired as biological information and QRS width is computed as a biological index indicative of a treatment effect by analyzing electrocardiograms. However, available biological information for identifying or determining the position of the lead-wire tip is not limited to electrocardiograms. For instance, a wall motion parameter acquired from an ultrasonic diagnostic image can be used for biological information.

A wall motion parameter is biological information acquired by tracking motion of myocardium through pattern matching. Specifically, a localized region for analyzing motion of myocardium is selected or set on the basis of an ultrasonic diagnostic image of a certain time phase out of respective ultrasonic diagnostic images acquired in plural time phases. The region corresponding to the selected localized region is identified in each of the ultrasonic diagnostic images of the other time phases, and motion of myocardium of the localized region between time phases is tracked (traced). A wall motion parameter can be computed by tracking change in position of myocardium of the localized region of each ultrasonic diagnostic image for each time phase. In other words, a wall motion parameter indicates moving amount of a position of myocardium.

CRT is treatment for asynchronous systole of atria and ventricles. A wall motion parameter indicates moving amount of a position of myocardium. Thus, a wall motion parameter is available as biological information indicative of asynchronous systole of atria and ventricles. The analysis function 324 of the medical image diagnostic apparatus 100 may extract each wall motion parameter from each of ultrasonic diagnostic images as biological information and compute each biological index indicative of a treatment effect for each position of the lead-wire tip on the basis of each biological index.

FIG. 16 is a schematic diagram illustrating a method of computing a biological index on the basis of a wall motion parameter in the second embodiment. FIG. 16 shows two graphs in each of which the horizontal axis indicates elapsed time and the vertical axis indicates a wall motion parameter. The upper part of FIG. 16 illustrates temporal change of a wall motion parameter in normal myocardium, and the lower part of FIG. 16 illustrates temporal change of a wall motion parameter in abnormal myocardium. The curved solid-line in each of the two graphs in FIG. 16 shows wall motion of myocardium of one localized region, i.e., wall motion of the first region. The curved broken-line in each of the two graphs in FIG. 16 shows wall motion of myocardium of another localized region, i.e., wall motion of the second region.

In the graph of the upper part of FIG. 16, the peak position of the curve line for the wall motion of the first region is almost the same time as the peak position of the curve line for the wall motion of the second region. Contrastively, in the graph of the lower part of FIG. 16, there is gap in peak position between the curve line for the wall motion of the first region and the curve line for the wall motion of the second region. The gap (i.e., difference or shift) in peak of wall motion indicates that myocardium motion is asynchronous between plural localized regions.

Thus, degree of gap in peak of a curved line indicating wall motion of myocardium of a localized region can be used as a biological index indicating a treatment effect in CRT, in a manner similar to the above-described QRS width in each electrocardiogram.

Note that not only ultrasonic diagnostic images but also MR images and CT images can be used for wall motion analysis of myocardium. In particular, MR images can be acquired for many time phases because there is no risk of exposure, and wall motion can be more accurately analyzed in the case of MR images than CT images. Additionally, it is possible to analyze wall motion in real time by using an interventional MRI apparatus, and in this case, one imaging apparatus can perform both of observation of inside of an object and acquisition of biological information.

According to the medical image diagnostic apparatus 100 of the second embodiment as described above, it is possible to easily determine an appropriate placement position of the lead-wire tip during an interventional operation on the basis of a biological index displayed in association with the position of the lead-wire tip.

Since a biological index indicative of a treatment effect is displayed in an intuitively recognizable manner such as a color map and a graph, the operating surgeon Q can easily determine an appropriate placement position of the lead-wire tip while operating the treatment device 19 such as the lead-wire tip. Additionally, since the optimum placement position can be easily determined, a surgery time can be reduced and exposure dose can be reduced.

THIRD EMBODIMENT

The above-described technique of specifying a treatment position in real time during an operative treatment is not limited to application to an interventional operation of placing a lead-wire tip in CRT but applied to other treatment or operation. In the third embodiment, a description will be given of a case where the above-described technique is applied to catheter ablation.

Catheter ablation is a surgical operation in which abnormal electric excitation occurring in respective parts of a heart is blocked by cauterizing apart of myocardium. In catheter ablation, plural parts of myocardium are cauterized in order by applying high-frequency current outputted from a tip of an ablation electrode. Generation positions of abnormal electric excitation and its transmission manner are different for each patient, and a treatment effect of catheter ablation is different depending on a part or parts to be cauterized. Since an operating surgeon performs catheter ablation while observing electrocardiograms and confirming an effect of ablation in conventional technology, many factors of catheter ablation in conventional technology depends on knowledge, skills, and experience of the operating surgeon similarly to CRT, which is one of factors that its surgical time is prolonged.

When the medical image diagnostic apparatus 100 is applied to catheter ablation, the treatment device 19 in FIG. 2 is ablation electrodes and the biological information acquisition apparatus 18 in FIG. 2 is an electrocardiograph.

As described above, an electrocardiogram includes two types which are a body-surface electrocardiogram and an intracardiac electrocardiogram. In catheter ablation, transmission of abnormal electric excitation occurring in respective parts of a heart is measured by measuring systole action of a localized myocardium. Thus, it is preferable that the biological information acquisition apparatus 18 is an electrocardiograph which can measure an intracardiac electrocardiogram.

Additionally, in the third embodiment, the analysis function 324 in FIG. 2 computes a biological index indicative of a treatment effect on the basis of intracardiac electrocardiograms which are biological information acquired by the biological information acquisition apparatus 18.

When systole action of myocardium is irregular, electric excitation generated in myocardium is transmitted through an irregular path. For instance, by comparing intracardiac electrocardiograms between a heart with normal systole and another heart in which irregular systole is generated, a waveform including plural peaks in one cycle of cardiac contraction (systole) and relaxation (diastole) is detected in each intracardiac electrocardiogram of the heart which is suffering from irregular systole.

In the third embodiment, the analysis function 324 computes a biological index on the basis of a waveform including plural peaks which indicate irregular systole action. In the case of normal myocardium, only one peak is observed in one cycle of cardiac systole and diastole in each intracardiac electrocardiogram. However, when two or more peaks are observed in one cycle of cardiac systole and diastole, the analysis function 324 may determine that systole action is abnormal. Additionally, for instance, the analysis function 324 may compute degree of irregular systole action in accordance with number of peaks.

Figure 17:
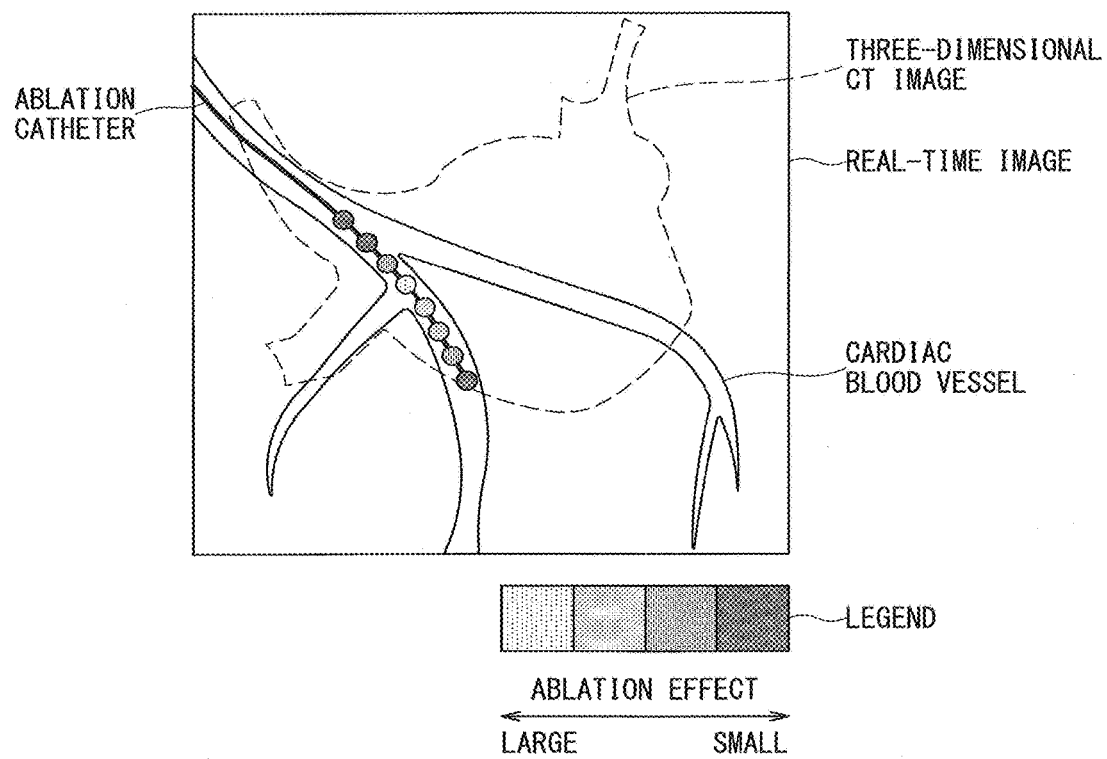
FIG. 17 is a schematic diagram illustrating one display aspect of a biological index in catheter ablation according to the third embodiment.

FIG. 17 is a schematic diagram illustrating one display aspect of a biological index in catheter ablation according to the third embodiment. In the case of FIG. 17, each biological index is superimposed and displayed by a color map on the position of the real-time image which corresponds to the myocardium cauterized by an ablation electrode, in accordance with the legend indicated at the bottom.

In the case of the color map in FIG. 17, a position with a higher ablation effect is more darkly (i.e., blackly) depicted for simplicity such that the ablation effect is distinguished by grayscale. Note that distinguishable display of ablation effects is not limited to grayscale. For instance, chromatic colors such as red, green, and blue are assigned to respective measured positions in accordance with the ablation effect thereof so that the ablation effect of each measured position is distinguishably displayed.

In FIG. 17, each measured position of myocardium cauterized by an ablation electrode is indicated by a circular figure which is filled with a color corresponding to the ablation effect of this position. For instance, each circular figure on a position of the ablation electrode is darkly displayed and indicates a high ablation effect. In this manner, the analysis function 324 computes ablation effects of respective ablation positions on the basis of number of peaks indicative of abnormal systole which are observed in each intracardiac electrocardiogram after being cauterized by an ablation electrode.

Note that a biological index in catheter ablation is not limited to number of peaks in each intracardiac electrocardiogram related to systole. For instance, a biological index may be computed on the basis of other factors such as an RR interval and P-wave width acquired from a body-surface electrocardiogram, electric potential of respective positions which can be measured from intracardiac electrocardiograms, and conduction time referred to as AH time from an A wave (i.e., atrial excitation of the His-bundle) to an H wave (i.e., electric potential of the His-bundle).

Since myocardium is cauterized by an ablation electrode, the analysis function 324 may compute influence of the cauterized myocardium on systole of the entire heart as the ablation effect, by comprehensively analyzing biological information acquired from intracardiac electrocardiograms and/or body-surface electrocardiograms. For instance, when all the numerical values of an RR interval, QRS width, and AH time are within respective predetermined ranges, the analysis function 324 may determine that the ablation effect is high. Conversely, when at least one of biological information items including an RR interval, QRS width, and AH time is not within its predetermined range, the analysis function 324 may determine that the ablation effect is low. The above-described predetermined range is, e.g., a normal value range of each of an RR interval, QRS width, and AH time.

Additionally or alternatively, the analysis function 324 may compute a biological index at a reference position and compute difference in biological index between the reference position and each position as the ablation effect.

Further, the medical image diagnostic apparatus 100 may simulate and store a treatment effect for each ablation position on the basis of biological information previously acquired by an electrophysiological examination. Accordingly, when myocardium is actually cauterized in an interventional operation, the medical image diagnostic apparatus 100 can display difference from the stored simulation result as a biological index.

Although a description has been given of the case where biological indexes are displayed by a color map in FIG. 17, the display aspects shown in FIG. 9 to FIG. 15 can also be applied to display of biological indexes in catheter ablation. The placement-position choice for the lead-wire tip described in FIG. 11 is replaced by an ablation-position choice in the case of catheter ablation.

Since biological indexes indicative of treatment effects of respective ablation positions in myocardium are displayed on a real-time image, the operating surgeon Q can instantly understand the effect of ablation. Additionally, by displaying a treatment effect in an intuitively recognizable manner, determination of the next ablation position and determination of completing the surgery are facilitated, which contributes to reduction in the surgery time and can reduce exposure dose by an X-ray fluoroscopic-imaging apparatus.

FOURTH EMBODIMENT

Artificial valve replacement for an aortic valve is also performed in an interventional operation. An artificial valve is a treatment device for treating backflow of blood caused by deterioration of a biological valve. Backflow of blood is remedied by attaching an artificial valve to a tip of a catheter and placing the artificial valve inside of an aortic blood vessel. When backflow of blood occurs from the placed artificial valve, the effect of the artificial valve is not sufficiently exerted. In conventional technology, an operating surgeon determines a placement position of an artificial valve based on his or her anatomical knowledge and experience while confirming the position of the artificial valve on, e.g., an ultrasonic diagnostic image acquired by using a transesophageal probe.

In the fourth embodiment, a description will be given of a case where the medical image diagnostic apparatus 100 is applied to artificial valve replacement. In the fourth embodiment, the treatment device 19 in FIG. 2 is an artificial valve and the biological information acquisition apparatus 18 in FIG. 2 is an ultrasonic diagnostic apparatus.

In the fourth embodiment, the analysis function 324 in FIG. 2 computes biological indexes indicative of a treatment effect on the basis of ultrasonic diagnostic images which are biological information acquired by the biological information acquisition apparatus 18. A biological index in artificial valve replacement is volume of regurgitant blood. It is possible to analyze a blood flow direction and blood flow velocity by using a color Doppler method as an imaging method of an ultrasonic diagnostic apparatus. The analysis function 324 extracts backflow vectors from the blood flow direction acquired by the color Doppler method, and computes biological indexes on the basis of distribution of backflow vectors.

The biological indexes computed by the analysis function 324 are displayed in association with the position of the artificial valve on each real-time image.

Figure 18:
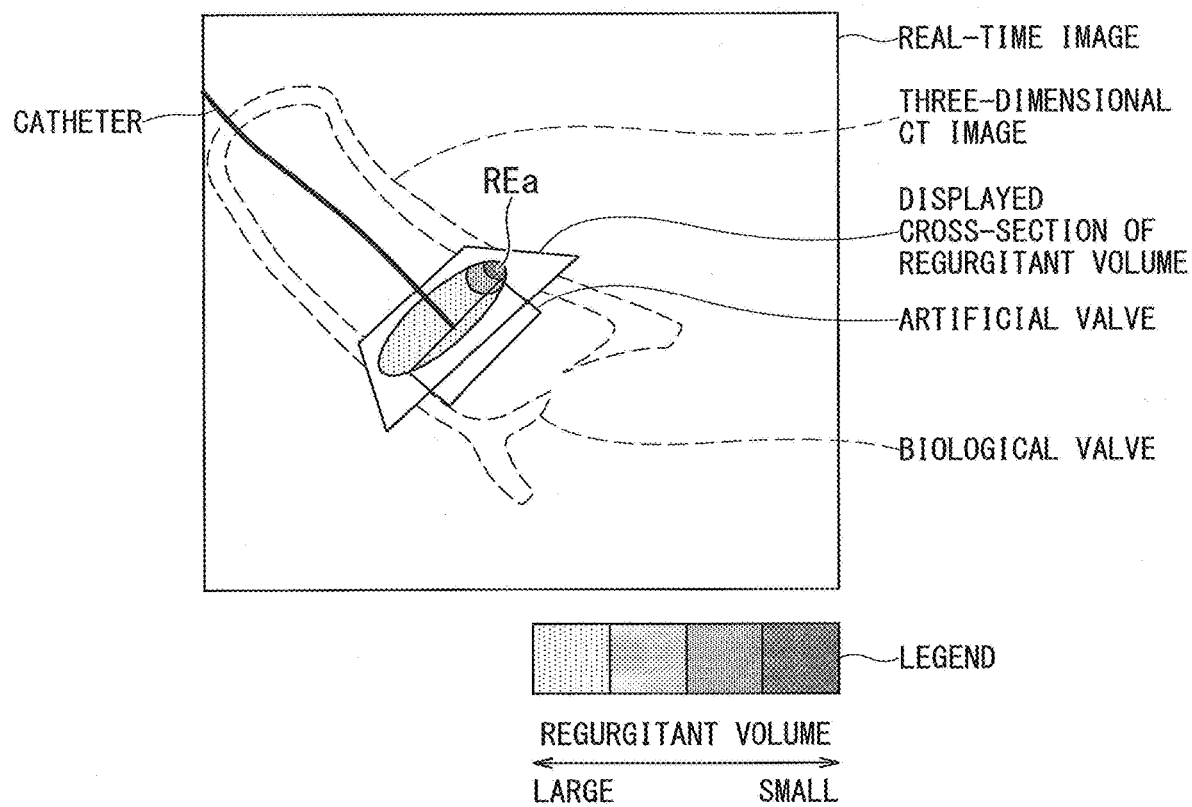
FIG. 18 is a schematic diagram illustrating one display aspect of a biological index in artificial valve replacement according to the fourth embodiment.

FIG. 18 is a schematic diagram illustrating one display aspect of a biological index in artificial valve replacement according to the fourth embodiment. In FIG. 18, according to the legend of the color map shown at the bottom, biological indexes are displayed as the color map on the real-time image at a position where the artificial valve is inserted.

In the case of the color map in FIG. 18, a position with larger volume of regurgitant blood is more darkly (i.e., blackly) depicted for simplicity such that volume of regurgitant blood is distinguished by grayscale. However, a distinguishable display aspect of volume of regurgitant blood is not limited to grayscale but chromatic colors such as red, blue, and green may be assigned as a distinguishable display aspect in accordance with volume of regurgitant blood.

FIG. 18 illustrates a case where the color map is displayed on a vascular cross-section at the current position of the artificial valve. A displayed cross-section of regurgitant volume maybe a cross-section which is perpendicular to the running direction of the aorta or be a cross-section which is in parallel with an attachment plane of the artificial valve.

In the case of FIG. 18, the region REa on the displayed cross-section of regurgitant volume is darkly depicted, which indicates large volume of regurgitant blood. The region around the center of the artificial valve is lightly depicted, which indicates small volume of regurgitant blood. For instance, the color map may be updated by computing regurgitant volume, each time the direction of the artificial valve is tilted or each time the artificial valve is moved.

Additionally, volume of regurgitant blood may be computed from real-time images. Specifically, biological information such as a blood flow direction and blood flow velocity can be acquired by administering a contract agent to the object P and measuring mobile velocity of the contrast agent from respective real-time images acquired at predetermined time intervals.

Further, volume of regurgitant blood can be computed by fluid-structure interaction analysis which is performed by inputting positional information of the artificial valve acquired from real-time images into a previously acquired image.

The fluid-structure interaction analysis is a method of computing pressure in a target blood vessel caused by blood flow on the basis of volume of blood flowing into the target blood vessel and volume of blood flowing out of the target blood vessel. It is possible to generate a vascular model of a blood vessel, which is a target of artificial valve replacement, from a previously acquired image. By inputting positional information of the artificial valve acquired from real-time images into the generated vascular model, it is possible to compute change in pressure in the target blood vessel caused by placement of the artificial valve. It is possible to compute volume of regurgitant blood at the placement position of the artificial valve from the change in pressure in the target blood vessel computed by the fluid-structure interaction analysis.

Note that a biological index indicative of a treatment effect in artificial valve replacement is not limited to volume of regurgitant blood. For instance, by using blood flow velocity anterior to and posterior to the artificial valve as biological information, pressure gradient may be computed as a biological index from blood flow velocity. In the case of aortic valve stenosis, blood volume pumped out of the left ventricle in increased in systole and thus pressure gradient between the left ventricle and the aorta is increased. As described above, pressure gradient is used for an index indicating degree of severity of valve stenosis. A treatment effect in artificial valve replacement may be determined on the basis of combination of pressure gradient and other biological information such as items pressure in a pulmonary blood vessel and valve area of a pulmonary blood vessel.

Although biological indexes are displayed by the color map in the case of FIG. 18, the display aspects shown in FIG. 9 to FIG. 15 can also be applied to display of biological indexes in artificial valve replacement. In the case of artificial valve replacement, the placement-position choice of the lead-wire tip in FIG. 11 is replaced by an artificial-valve placement-position choice.

In the fourth embodiment as described above, it is possible to determine an appropriate placement position of the artificial valve on the basis of information except anatomical knowledge by displaying biological indexes on each real-time image in accordance with change in position and/or direction of the artificial valve. Additionally, by displaying biological indexes in an intuitively recognizable manner, it is possible to assist an operating surgeon in determining an appropriate placement position of an artificial valve. This advantage contributes to reduction in the surgery time, and exposure dose can be reduced in the case of using an X-ray fluoroscopic-imaging apparatus.

Although a description has been given of artificial valve replacement for an aortic valve, a mitral clip in the form of a clip is used as the treatment device 19 in the case of surgery of a mitral valve. In treatment of a mitral valve, backflow of blood is prevented by clipping biological valves with the clip-shaped treatment device 19. Although treatment of a mitral valve differs from treatment of an aortic valve in terms of treatment method and type of the treatment device 19, the same biological indexes indicating a treatment effect as treatment of an aortic valve can be used for treatment of a mitral valve.

FIFTH EMBODIMENT

In the fifth embodiment, a description will be given of a case where the medical image diagnostic apparatus 100 is applied to stent placement with the use of a catheter.

A stent is the treatment device 19 which treats stenosis of a blood vessel such as a cerebral blood vessel, a carotid artery, and a cardiac blood vessel. When the medical image diagnostic apparatus 100 is applied to treatment for vascular stenosis with the use of a stent, the treatment device 19 is a stent and a biological index indicative of a treatment effect is blood flow volume and/or blood flow velocity acquired by an ultrasonic diagnostic apparatus or FFR (Fractional Flow Reserve) computed by fluid-structure interaction analysis.

FFR is an index for estimating degree of interruption of blood flow in a blood vessel which lies downstream of the stenosed blood vessel. FFR is computed by estimating pressure applied to blood vessels anterior to and posterior to the stenosed blood vessel under the fluid-structure interaction analysis.

On the basis of magnitude of the computed FFR which is a biological index, for instance, a color map and/or a numerical value shown in FIG. 8 and/or FIG. 9 may be displayed on a position of each real-time image where the stent exists. Additionally, change in FFR may be displayed as a graph for each position where a stent exist in a manner similar to FIG. 10, and a stent placement-position choice may be displayed in a manner similar to FIG. 11.

Types of stent regarding its length and diameter to be placed inside a blood vessel is determined on the basis of, e.g., a previously acquired image at the planning phase prior to surgery. Thus, the medical image diagnostic apparatus 100 may be configured to display an estimated biological index in the case of placing a stent, which is determined to be used in the surgery according to the surgical plan, at the stenosed position before actually inserting this stent into inside of the blood vessel using a catheter. Additionally, the respective components of the medical image diagnostic apparatus 100 maybe configured to change length and/or diameter of a stent and display assistance information such as a biological index estimated from the changed condition.

Stent placement is treatment of resolving stenosis and recovering blood flow in the downstream of the stenosed blood vessel. Thus, a biological index may be computed for the blood vessel in the downstream of the stent on the basis of FFR, blood flow velocity, or blood flow volume of this downstream blood vessel so that the computed biological index is displayed on this downstream blood vessel of the displayed image.

Although a description has been given of the case where the medical image diagnostic apparatus 100 includes the imaging apparatus 10 in the above-described embodiments, this is only one aspect. Configuration consisting of only the medical image processing apparatus 30 unequipped with the imaging apparatus 10 can obtain the same effects as the medical image diagnostic apparatus 100, by acquiring real-time images and previously acquired images from the imaging apparatus 10 and/or the image server 200.

According to the medical image diagnostic apparatus 100 and the medical image processing apparatus 30 of at least one of the above-described embodiments, a treatment target position can be more easily specified than conventional technology.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image diagnostic apparatus comprising:
   an imaging apparatus configured to acquire medical images of an object at respective time phases;
   a memory circuit;
   a display; and
   processing circuitry configured to
      detect respective positions of a treatment device in the medical images,
      acquire biological information from the medical images,
      compute biological indexes, each of which indicates degree of a treatment effect, for the respective time phases based on the biological information,
      cause the memory circuit to store the biological indexes and the respective positions of the treatment device in the medical images in such a manner that each biological index is associated with a position of the treatment device in a medical image, from which the biological information corresponding to the each biological index is acquired, for the respective time phases, and
      cause the display to display each position of the treatment device and a biological index associated with the each position of the treatment device.

2. The medical image diagnostic apparatus according to claim 1,
   wherein the processing circuitry is configured to compute the biological indexes corresponding to respective positions on a moving trace of the treatment device, by analyzing plural sets of biological information acquired for the respective positions on the moving trace of the treatment device; and
   the display is configured to superimpose and display the biological indexes on the respective positions on the moving trace of the treatment device.

3. The medical image diagnostic apparatus according to claim 1,
   wherein the display is configured to superimpose and display the biological indexes on respective positions on a moving trace of the treatment device in such a manner that a display aspect is different for each biological index.

4. The medical image diagnostic apparatus according to claim 2,
   wherein the display is configured to display the respective positions on the moving trace of the treatment device in chromatic colors, which are assigned to the respective positions on the moving trace of the treatment device depending on difference in biological index.

5. The medical image diagnostic apparatus according to claim 1,
   wherein the processing circuitry is configured to compute an appropriate placement position of the treatment device based on the biological indexes; and
   the display is configured to display the appropriate placement position of the treatment device.

6. The medical image diagnostic apparatus according to claim 1,
   wherein the processing circuitry is configured to
      treat each of the medical images as a first medical image,
      treat a medical image, which is acquired by imaging a same object as the first medical image before acquisition of the first medical image, as a second medical image, and
      perform positioning between the first medical image and the second medical image; and
   the display is configured to superimpose and display at least one biological index on at least one of the first medical image and the second medical image.

7. The medical image diagnostic apparatus according to claim 6,
   wherein the second medical image is four-dimensional image data including three-dimensional image and time phase data of the three-dimensional image; and
   the processing circuitry is configured to synchronize the first medical image with the second medical image based on the time phase data.

8. The medical image diagnostic apparatus according to claim 6,
   wherein the display is configured to display the first medical image and the second medical image in parallel.

9. The medical image diagnostic apparatus according to claim 6,
   wherein the second medical image is an image obtained by performing volume rendering processing on the four-dimensional image data; and the display is configured to superimpose and display the biological indexes on respective positions on a moving trace of the treatment device on the second medical image.

10. The medical image diagnostic apparatus according to claim 6,
wherein the second medical image is an image obtained by performing curved MPR (Multi Planer Reconstruction) processing on four-dimensional image data; and
the display is configured to superimpose and display the biological indexes on respective positions on a moving trace of the treatment device on the second medical image.

11. The medical image diagnostic apparatus according to claim 1,
wherein the display is configured to display respective biological indexes computed based on plural sets of biological information, the plural sets of biological information being acquired from respective acquisition periods.

12. The medical image diagnostic apparatus according to claim 6,
wherein the processing circuitry is configured to
extract an anatomically characteristic part of at least one of an atrium, a ventricle, a coronary vein, an aorta, an aortic valve, and a mitral valve, and
perform the positioning between the first medical image and the second medical image based on the anatomically characteristic part.

13. The medical image diagnostic apparatus according to claim 1,
wherein the processing circuitry is configured to extract at least one of a lead-wire tip of an implantable defibrillator, a tip of an ablation catheter, a stent, an artificial valve, and a mitral clip, as the treatment device.

14. The medical image diagnostic apparatus according to claim 6,
wherein the processing circuitry is configured to compute the biological indexes based on biological information which is acquired from at least one of an electrocardiogram, an ultrasonic image, and the second medical image.

15. A medical image processing apparatus comprising:
a memory circuit;
a display; and
processing circuitry configured to
acquire medical images of an object at respective time phases,
detect respective positions of a treatment device in the medical images,
acquire biological information from the medical images,
compute biological indexes, each of which indicates degree of a treatment effect, for the respective time phases based on the biological information,
cause the memory circuit to store the biological indexes and the respective positions of the treatment device in the medical images in such a manner that each biological index is associated with a position of the treatment device in a medical image, from which the biological information corresponding to the each biological index is acquired, for the respective time phases, and
cause the display to display each position of the treatment device and a biological index associated with the each position of the treatment device.

* * * * *